(12) United States Patent
Fram

(10) Patent No.: US 10,134,126 B2
(45) Date of Patent: *Nov. 20, 2018

(54) INTELLIGENT DYNAMIC PRELOADING AND PROCESSING

(71) Applicant: D.R. Systems, Inc., San Diego, CA (US)

(72) Inventor: Evan K. Fram, Paradise Valley, AZ (US)

(73) Assignee: D.R. Systems, Inc., San Diego, CA (US)

( * ) Notice: Subject to any disclaimer, the term of this patent is extended or adjusted under 35 U.S.C. 154(b) by 115 days.

This patent is subject to a terminal disclaimer.

(21) Appl. No.: 15/074,268

(22) Filed: Mar. 18, 2016

(65) Prior Publication Data

US 2017/0039701 A1    Feb. 9, 2017

Related U.S. Application Data

(63) Continuation of application No. 14/488,166, filed on Sep. 16, 2014, now Pat. No. 9,323,891, which is a
(Continued)

(51) Int. Cl.
| | |
|---|---|
| *G06K 9/00* | (2006.01) |
| *G06T 7/00* | (2017.01) |
| *G06F 19/00* | (2018.01) |
| *A61B 5/00* | (2006.01) |
| *G06K 9/52* | (2006.01) |
| *G06K 9/62* | (2006.01) |
| *G06N 7/00* | (2006.01) |
| *G06T 7/20* | (2017.01) |

(52) U.S. Cl.
CPC .......... *G06T 7/0012* (2013.01); *A61B 5/7271* (2013.01); *A61B 5/742* (2013.01); *G06F 19/321* (2013.01); *G06K 9/52* (2013.01); *G06K 9/6201* (2013.01); *G06N 7/005* (2013.01); *G06T 7/20* (2013.01); *G06T 2207/30004* (2013.01); *G06T 2207/30196* (2013.01)

(58) Field of Classification Search
CPC ..... A61B 5/7271; A61B 5/742; G06F 19/321; G06K 9/52; G06K 9/6201; G06N 7/005; G06T 2207/30004; G06T 2207/30196; G06T 7/0012; G06T 7/20
See application file for complete search history.

(56) References Cited

U.S. PATENT DOCUMENTS

| | | |
|---|---|---|
| 5,452,416 A | 9/1995 | Hilto et al. |
| 5,767,854 A | 6/1998 | Anwar |

(Continued)

OTHER PUBLICATIONS

U.S. Appl. No. 13/624,791, filed Sep. 21, 2012 including its ongoing prosecution history, including without limitation Office Actions, Amendments, Remarks, and any other potentially relevant documents.

(Continued)

*Primary Examiner* — Nirav G Patel
(74) *Attorney, Agent, or Firm* — Michael Best & Friedrich LLP

(57) ABSTRACT

Provided herein are various systems and methods of adjusting images of an image series that are preloaded (and/or otherwise processed) in view of behavior data associated with viewing of other previous exams having similar characteristics (e.g., same modality) and/or by the same user.

20 Claims, 17 Drawing Sheets

Related U.S. Application Data continuation of application No. 13/624,791, filed on Sep. 21, 2012, now Pat. No. 8,867,807.

(60) Provisional application No. 61/538,609, filed on Sep. 23, 2011.

(56) References Cited

U.S. PATENT DOCUMENTS

| | | | |
|---|---|---|---|
| 7,685,262 | B2 | 3/2010 | Choubey et al. |
| 8,019,626 | B2 | 9/2011 | Mahesh et al. |
| 8,078,749 | B2 | 12/2011 | Khosravy |
| 8,543,415 | B2 | 9/2013 | Venon et al. |
| 8,867,807 | B1 | 10/2014 | Fram |
| 9,323,891 | B1 | 4/2016 | Fram |
| 2003/0005140 | A1 | 1/2003 | Dekel et al. |
| 2004/0077952 | A1 | 4/2004 | Rafter et al. |
| 2004/0095349 | A1 | 5/2004 | Bito et al. |
| 2004/0136404 | A1 | 7/2004 | Mahonen et al. |
| 2004/0146221 | A1 | 7/2004 | Siegel et al. |
| 2005/0108060 | A1 | 5/2005 | Sasano |
| 2006/0007244 | A1 | 1/2006 | Matsumoto |
| 2006/0093207 | A1 | 5/2006 | Reicher et al. |
| 2006/0170954 | A1 | 8/2006 | Leyvi |
| 2006/0190572 | A1 | 8/2006 | Novik et al. |
| 2006/0215569 | A1 | 9/2006 | Khosravy et al. |
| 2006/0230067 | A1 | 10/2006 | Tarnoff et al. |
| 2007/0053567 | A1 | 3/2007 | Adachi et al. |
| 2007/0106683 | A1 | 5/2007 | Grabelsky et al. |
| 2008/0069397 | A1 | 3/2008 | Bartsch |
| 2009/0089448 | A1 | 4/2009 | Sze et al. |
| 2009/0182577 | A1 | 7/2009 | Squilla et al. |
| 2010/0131294 | A1 | 5/2010 | Venon et al. |
| 2011/0231209 | A1 | 9/2011 | Maresh et al. |
| 2012/0095953 | A1 | 4/2012 | Schmidt et al. |
| 2012/0124517 | A1 | 5/2012 | Landry et al. |

OTHER PUBLICATIONS

U.S. Appl. No. 14/488,166, filed Sep. 16, 2014, including its ongoing prosecution history, including without limitation Office Actions, Amendments, Remarks, and any other potentially relevant documents, Fram.
U.S. Appl. No. 13/495,991, filed Jun. 13, 2012, including its ongoing prosecution history, including without limitation Office Actions, Amendments, Remarks, and any other potentially relevant documents, Fram.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.

(56) References Cited

OTHER PUBLICATIONS

Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQubec%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
PHILIPS, IntelliSpace: Multi-modality tumor tracking application versus manual PACS methods, A time study for Response Evaluation Criteria in Solid Tumors (RECIST). 2012, Koninklijke Philips Electronics N.V., in four pages.
PHILIPS IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power-Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Pre-Appeal Decision from the U.S. Patent and Trademark Office for U.S. Appl. No. 13/495,991 dated Dec. 13, 2016 (2 pages).
Non-Final Office Action from the U.S. Patent and Trademark Office for U.S. Appl. No. 13/495,991 dated Nov. 6, 2014 (10 pages).
Non-Final Office Action from the U.S. Patent and Trademark Office U.S. Appl. No. 13/495,991 dated Sep. 21, 2015 (5 pages).
Non-Final Office Action from the U.S. Patent and Trademark Office for U.S. Appl. No. 13/495,991 dated Aug. 11, 2016 (12 pages).
Final Office Action from the U.S. Patent and Trademark Office for U.S. Appl. No. 13/495,991 dated Apr. 15, 2014 (12 pages).
Final Office Action from the U.S. Patent and Trademark Office for U.S. Appl. No. 13/495,991 dated Mar. 19, 2015 (12 pages).
Final Office Action from the U.S. Patent and Trademark Office for U.S. Appl. No. 13/495,991 dated Feb. 18, 2016 (10 pages).
Examiner's Answer from the U.S. Patent and Trademark Office for U.S. Appl. No. 13/495,991 dated Apr. 7, 2017 (18 pages).
Applicant-Initiated Interview Summary from the U.S. Patent and Trademark Office for U.S. Appl. No. 13/495,991 dated Mar. 13, 2014 (3 pages).
Applicant-Initiated Interview Summary from the U.S. Patent and Trademark Office for U.S. Appl. No. 13/495,991 dated Jun. 18, 2014 (3 pages).
Applicant-Initiated Interview Summary from the U.S. Patent and Trademark Office for U.S. Appl. No. 13/495,991 dated Apr. 16, 2015 (3 pages).
Applicant-Initiated Interview Summary from the U.S. Patent and Trademark Office for U.S. Appl. No. 13/495,991 dated May 6, 2016 (3 pages).
Notice of Allowance from the U.S. Patent and Trademark Office for U.S. Appl. No. 14/488,166 dated Dec. 23, 2015 (7 pages).
Non-Final Office Action from the U.S. Patent and Trademark Office for U.S. Appl. No. 14/488,166 dated Sep. 25, 2015 (12 pages).

(56) References Cited

OTHER PUBLICATIONS

Notice of Allowance from the U.S. Patent and Trademark Office for U.S. Appl. No. 13/624,791 dated Jun. 20, 2014 (7 pages).
Non-Final Office Action from the U.S. Patent and Trademark Office for U.S. Appl. No. 13/624,791 dated Feb. 19, 2014 (16 pages).

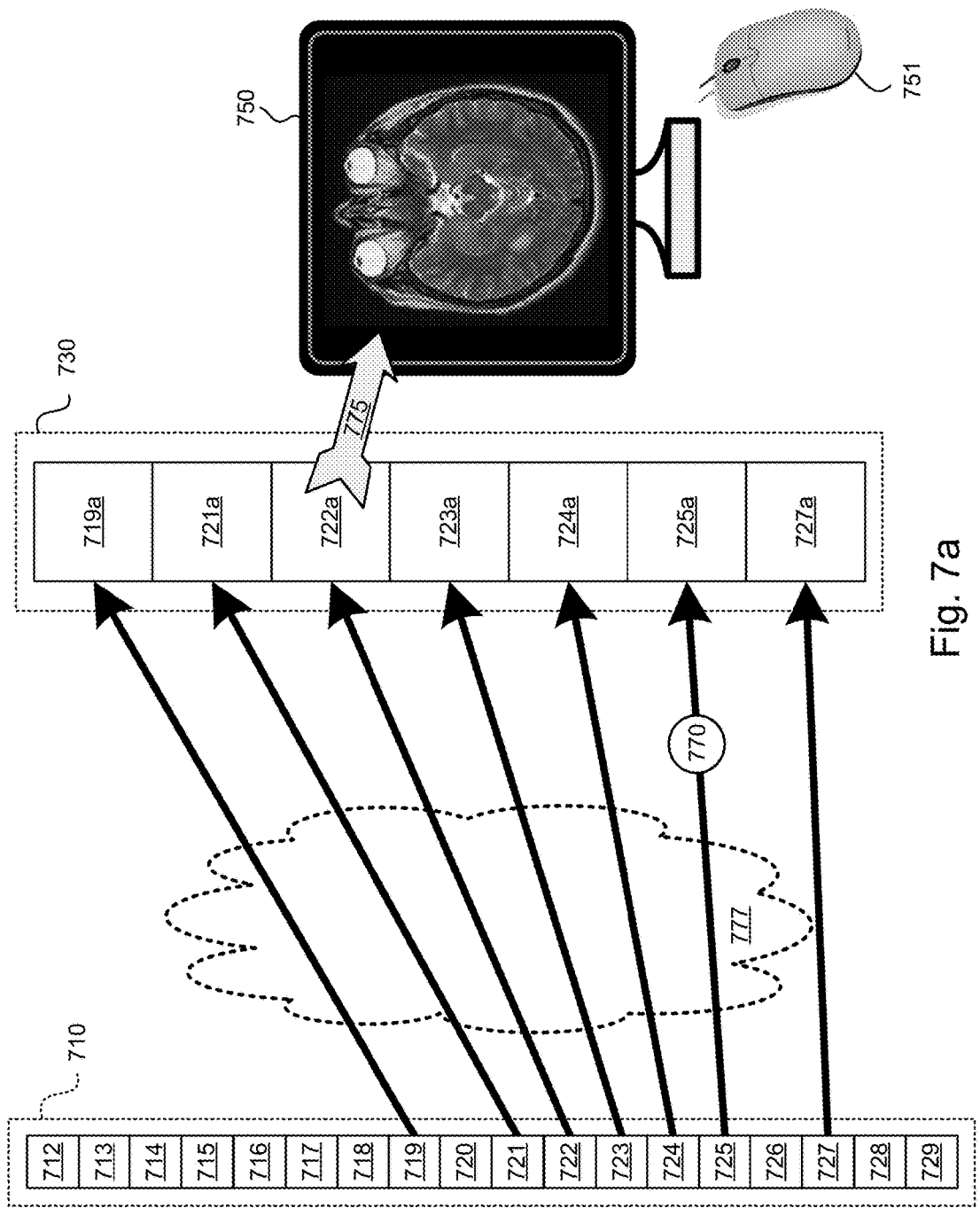

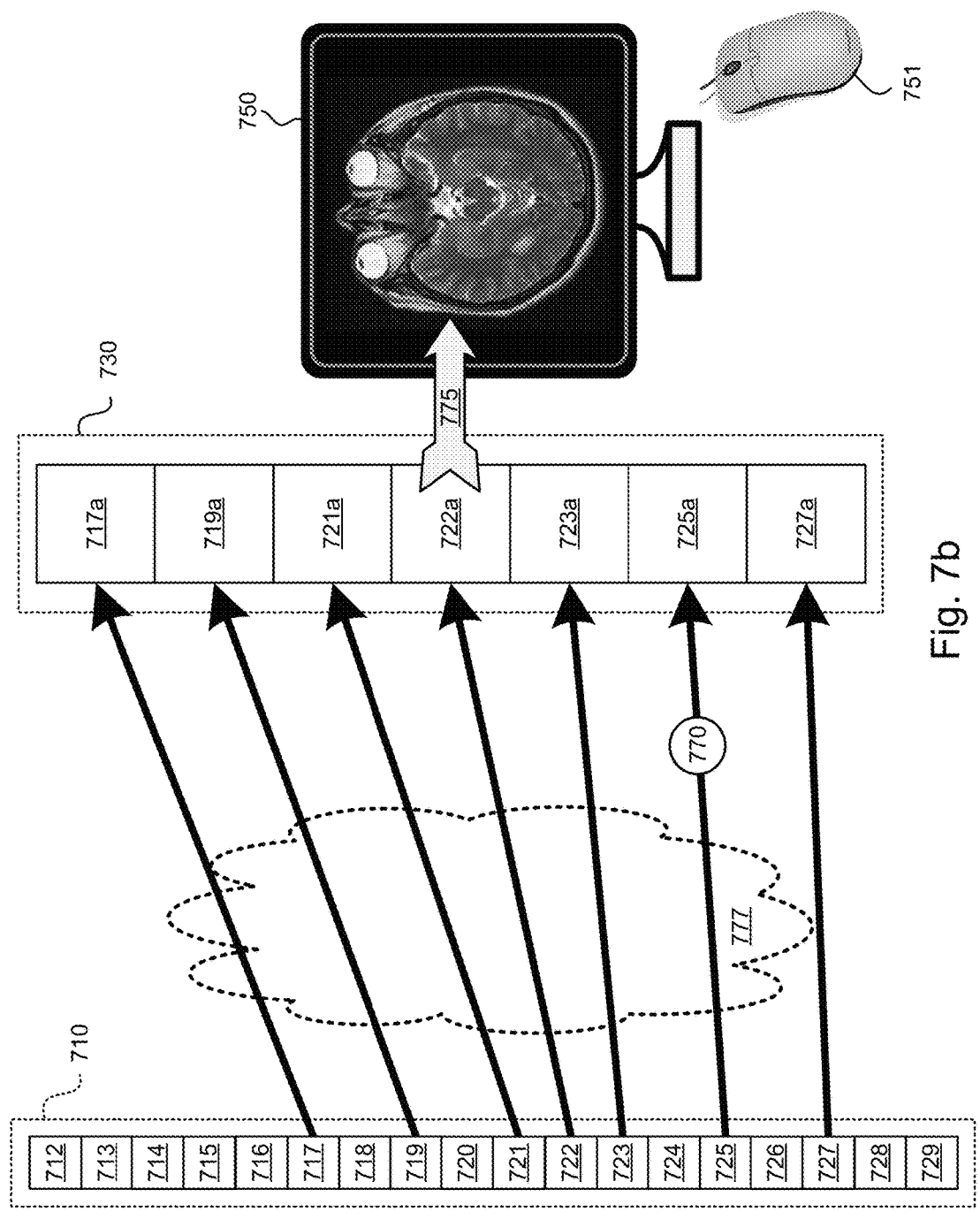

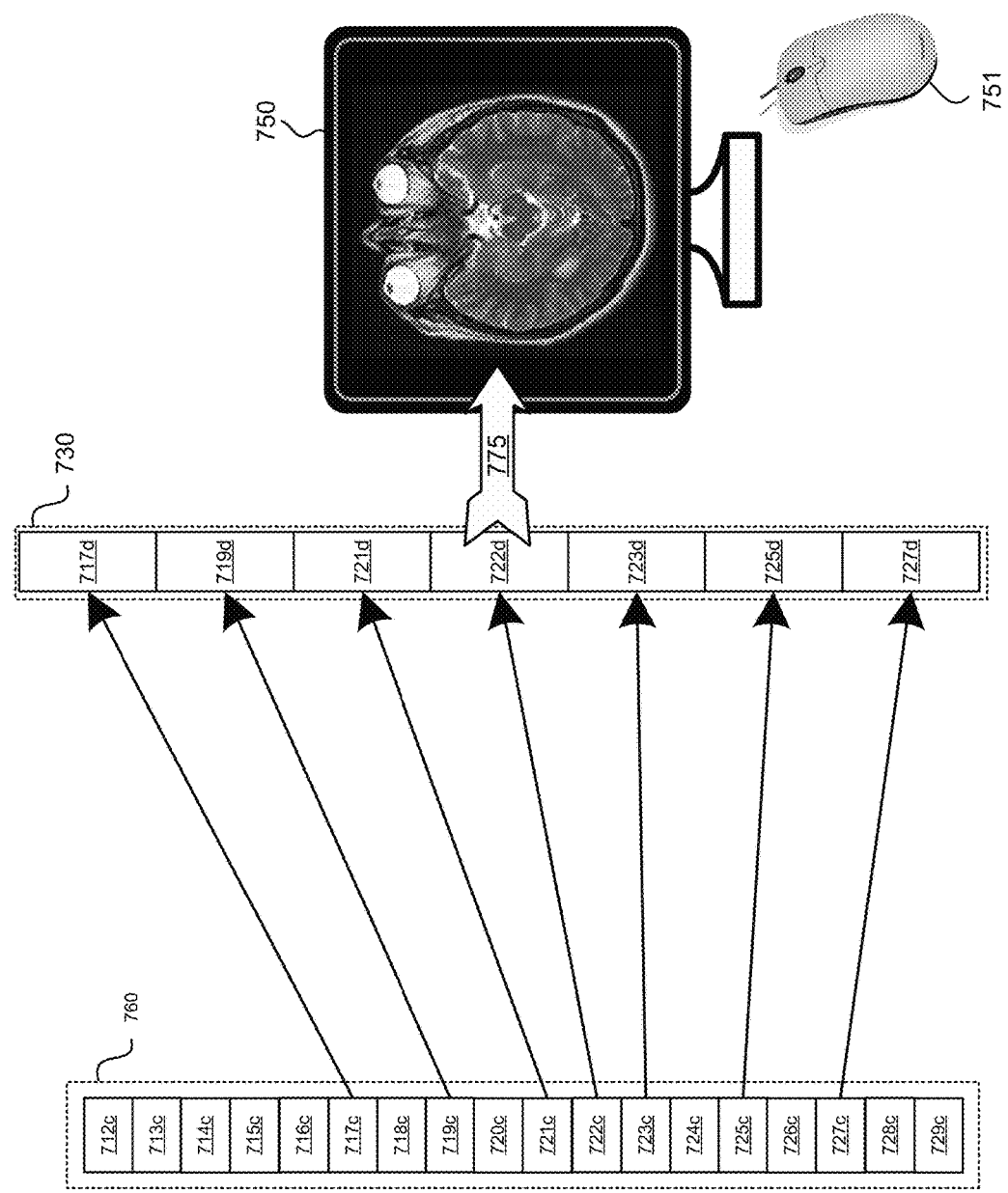

INTELLIGENT DYNAMIC PRELOADING AND PROCESSING

CROSS-REFERENCE TO RELATED APPLICATIONS

This application is a continuation of U.S. application Ser. No. 14/488,166, filed Sep. 16, 2014, which is a continuation of U.S. application Ser. No. 13/624,791, filed Sep. 21, 2012, which claims the benefit of priority under 35 U.S.C. § 119(e) of U.S. Provisional Application No. 61/538,609, filed Sep. 23, 2011. All of the above-referenced items are hereby incorporated by reference herein in their entireties.

BACKGROUND

Doctors use computing devices to view medical imaging exams that may include hundreds or even thousands of images. The images being viewed may be communicated to the physician's computing device from a remote location via a LAN, a WAN, the Internet, a cellular data connection, or other means for digital communication. Efficient interpretation requires that images be very rapidly available and that navigation from image to image be rapid.

SUMMARY

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In one embodiment, a method of processing images comprises determining, by a computing system having one or more computer processors, a first characteristic of a first image series comprising a plurality of medical images, monitoring, by the computing system, behavior of a user in displaying images of the first images series, including recording behavior data indicating an order in which images of the first image series are accessed by the user, and analyzing the behavior data in order to determine a model usable to predict respective probabilities of images at various adjacency offsets from a particular image being displayed next, after display of the particular image.

In one embodiment, the model indicates that a first image having a higher adjacency offset than a second image is more likely to be displayed within the predetermined time period. In one embodiment, more than one of the images has substantially identical respective probabilities of being displayed next, after display of the particular image. In one embodiment, the first characteristic comprises one or more of exam type, modality, clinical information, clinical history of a patient, region of body depicted in the first image series, technical parameters of the first image series, whether the images were obtained with or without intravenous contrast. In one embodiment, the model is associated with one or more characteristics of a display device on which the images are displayed, a user identity, user group, or user role of the user. In one embodiment, the technical parameters comprise one or more of series type, whether the images series is a 2D or a volumetric acquisition, slice thickness, resolution, image size, or image type. In one embodiment, the series type comprises one or more of primary acquisition, MPR (multiplanar reconstruction), MIP (maximum intensity projection), or 3D volume rendering.

In one embodiment, the model comprises a first model and a second model that are configured to predict probabilities of images being display next with reference to respective portions of image series having the first characteristic. In one embodiment, the first model is configured for use while a user is displaying images within a predetermined initial portion of the image series. In one embodiment, the second model is configured for use while the user is displaying images outside of the predetermined initial portion of the image series. In one embodiment, the first model is configured for use while the user is displaying images of a first anatomical feature. In one embodiment, the second model is configured for use while the user is displaying images of a second anatomical feature.

In one embodiment, the method further comprises receiving a request for display of a second image series, and in response to determining that a second characteristic of the second image series substantially matches the first characteristic of the first image series, selecting the model for use in determining images of the second image series to preload. In one embodiment, determining images of the second image series to preload comprises, for respective displayed images, comprises determining, based on the model, one or more images to preload into a local memory of the computing device on which the respective image is displayed, determining which of the one or more images to preload are already stored in the local memory, and initiating preloading of any of the one or more images to preload that are not already stored in the local memory. In one embodiment, the model is stored in a data structure with an association between the model and the first characteristic. In one embodiment, the data structure further stores an association between the model and the user or a group of users, wherein the model is selected for use in determining images of the second image series to preload only if a user requesting display of the second image series is the user or in the user group associated with the model.

In one embodiment, a method comprises receiving a request for processing of an image series, determining, by a computing system having one or more hardware processors, a characteristic of the image series, the computing system, and/or a user operating the computing system, wherein the characteristic is usable to select an appropriate processing model, selecting, by the computing system, a processing model associated with the determined characteristic, wherein the processing model is determined based on previously monitored behavior of one or more users in processing of one or more other image series having the same or similar determined characteristic, wherein the processing model indicates respective probabilities of images at various adjacency offsets from a particular image being processed next, after processing of the particular image, and applying, by the computing system, the selected processing model in order to optimize processing of the image series.

In one embodiment, processing of the image series comprises one or more of preloading images into a local memory, decompressing images, performing computer aided diagnosis, or reconstructing images. In one embodiment, reconstructing images comprises one or more of MPR (multiplanar reconstruction), MIP (maximum intensity projection), or 3D volume rendering. In one embodiment, the characteristic of the image series comprises one or more of series type, series description, exam type, modality, clinical information, clinical history of a patient, region of body depicted in the image series, technical parameters of the image series, or whether the images were obtained with or without intravenous contrast. In one embodiment, the characteristics of the computing system comprise one or more of a characteristic of a display device on which the images are displayed or a processing speed of the computing system. In one embodiment, the characteristics of the user comprise one or more of a user role, a user group, or type of physician associated with the image series. In one embodiment, the processing model is associated with a user of the computing system and/or a user group of which the user is a member. In one embodiment, the request for processing comprises a user of the computing system requesting display of one or more of the images of the image series. In one embodiment, the request for processing comprises a request to preload images of the image series into a local memory of the computing system.

BRIEF DESCRIPTION OF THE DRAWINGS

FIGS. 7a and 7b are block diagrams illustrating example transfers of images from remote image storage to a memory buffer in accordance with behavior data of a user.

FIG. 7c is a block diagram illustrating an example decompression of images from a storage device (remote or local) to a memory buffer in accordance with a processing model.

FIG. 9b is a block diagram illustrating preloading of images from linked image series, such as the image series including the images discussed with reference to FIG. 9a.

DETAILED DESCRIPTION

Figure 1:
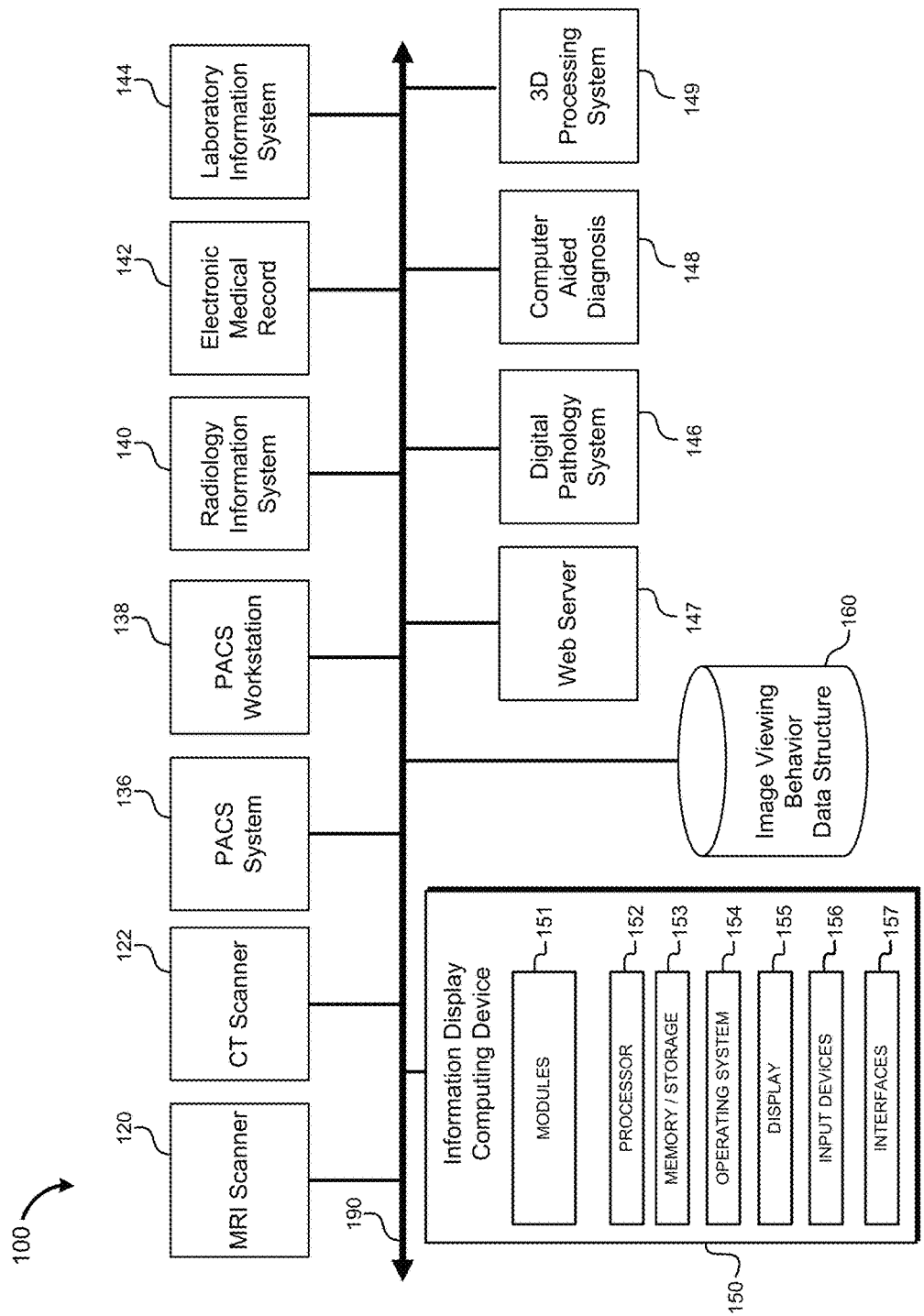
FIG. 1 is a system diagram that shows the various components of a system for displaying information utilizing certain systems and methods described herein.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a tangible computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Introduction

Systems and methods described herein may improve performance of computing systems that display medical images (or other images) by intelligently processing the images (e.g., requesting, preloading, constructing, modifying, etc.) based on the prior image viewing behavior of the user or a group of users. In some embodiments, the systems and methods described herein monitor how users navigate through various images within medical imaging exams to determine characteristics of their behavior in displaying images. This information, which is referred to herein as behavior data, user behavior data, or viewing behavior data, may then be used to prioritize the order of image communication and/or processing to improve the speed of image access and improve user efficiency.

While the systems and methods described herein will be illustrated with medical imaging information, the systems and methods described herein may be utilized to manage nonmedical information as well as digital information other than images.

Systems and methods described herein may be advantageous in many settings, for example:

- Where system responsiveness is limited by the speed of processing of digital data
- Where system responsiveness is limited by available communication bandwidth
- Where buffering and/or preprocessing of digital data is limited by the amount of fast local memory
- In conjunction with multimedia data such as images, video and/or sound
- In computer programs, apps, webApps, and internet browsers Medical imaging exams can be acquired by a number of different medical imaging techniques, including computed tomography (CT), magnetic resonance imaging (MRI), ultrasound, nuclear medicine, positron emission computed tomography (PET), digital angiography, mammography, computed radiography, digital radiography, fluoroscopy, and others. In addition, systems and methods described herein may be used for images acquired in other areas of medicine, such as pathology, dermatology, and endoscopy, as well as images associated with fields outside of medicine. Doctors viewing medical imaging exams typically view them on computing devices that may be, for example, configured to communicate with a Picture Archive and Communication System (PACS), Electronic Medical Record (EMR), or online Personal Health Record Systems (PHR). Computing devices used to view medical imaging exams, such as by a doctor, comprise a wide range of devices including PACS workstations, personal computers, tablet computers, PDAs, smartphones, and others. Medical imaging exams may be stored on a computer server and transferred to the computing device used by the doctor to view the exam, for example, using a LAN, WAN, the Internet, a cellular data connection or other wireless connection, or physical media such as a CD, DVD, or flash memory device.

Often the speed of transfer via a network or from physical media is too slow for sufficiently rapid display of images. For example, radiologists may desire to view a series of 2 megabyte images at a rate of 15 images/second to accurately interpret the exam. Since transmission of the images from a remote server may be too slow to support that speed, images may be stored in local fast computer memory, such as RAM, FLASH memory, or disc drive. Local storage of images may have one or more of several advantages:

- With images preloaded into local memory they can be rapidly displayed on demand.
- In the course of viewing a medical imaging exam, doctors may display images within the exam multiple times as they examine different structures and/or display the images with different display parameters. When images are stored in memory local to the computing system used for image display, the images may not need to be retrieved multiple times from the remote server, decreasing server and network utilization.
- Images can be retrieved and stored in memory while the user is viewing other images.

While loading images into memory may have advantages, the available memory may be insufficient for a number of reasons, including:

- Limited physical memory
- Operating System limitations that restrict the addressable memory
- Limited memory available to the program displaying the images, for example because of limitations in the software model, e.g. browser, or usage of memory by other programs or processes.

There is a need for new techniques for handling medical imaging data that overcome these problems and increase the efficiency and speed of managing medical imaging exams. Systems and methods described herein are used to determine the priority of image retrieval and processing. These systems and methods are usable for other image types (e.g., not medical images, such as surveillance images, satellite images, etc.) in the same or similar manner as discussed herein with reference to medical images. Thus, any reference herein to medical images should be construed to cover non-medical images as well.

In many scenarios users view or otherwise utilize large amounts of data. For example, in the course of viewing an online movie, a gigabyte or more of information may be transferred to the user's computing device via the internet, cellular data network, or other means of electronic communication. Similarly, in the course of viewing a medical imaging exam, a gigabyte or more of information may be transferred to a doctor's computing device.

In order for the user to more efficiently view various portions of large datasets, for example video frames of a movie or images within a medical imaging exam, the data to be viewed next by the user should be rapidly available, either by being stored locally or available for fast transfer from remote storage.

One solution would be to download the entire dataset to the user's computing device in advance of the user needing it, but this may be impractical due to bandwidth and/or local storage limitations. For example, the time to transfer an entire movie prior to viewing may be unacceptably long. In addition, the entire dataset may be too large to store locally in the computing device. Instead, the data may be transferred to the user's computing device while the user is consuming it. In the case of a user viewing a movie, the process of transferring data may be straightforward in that the user typically views the information within the movie in order from beginning to end.

Figure 4:
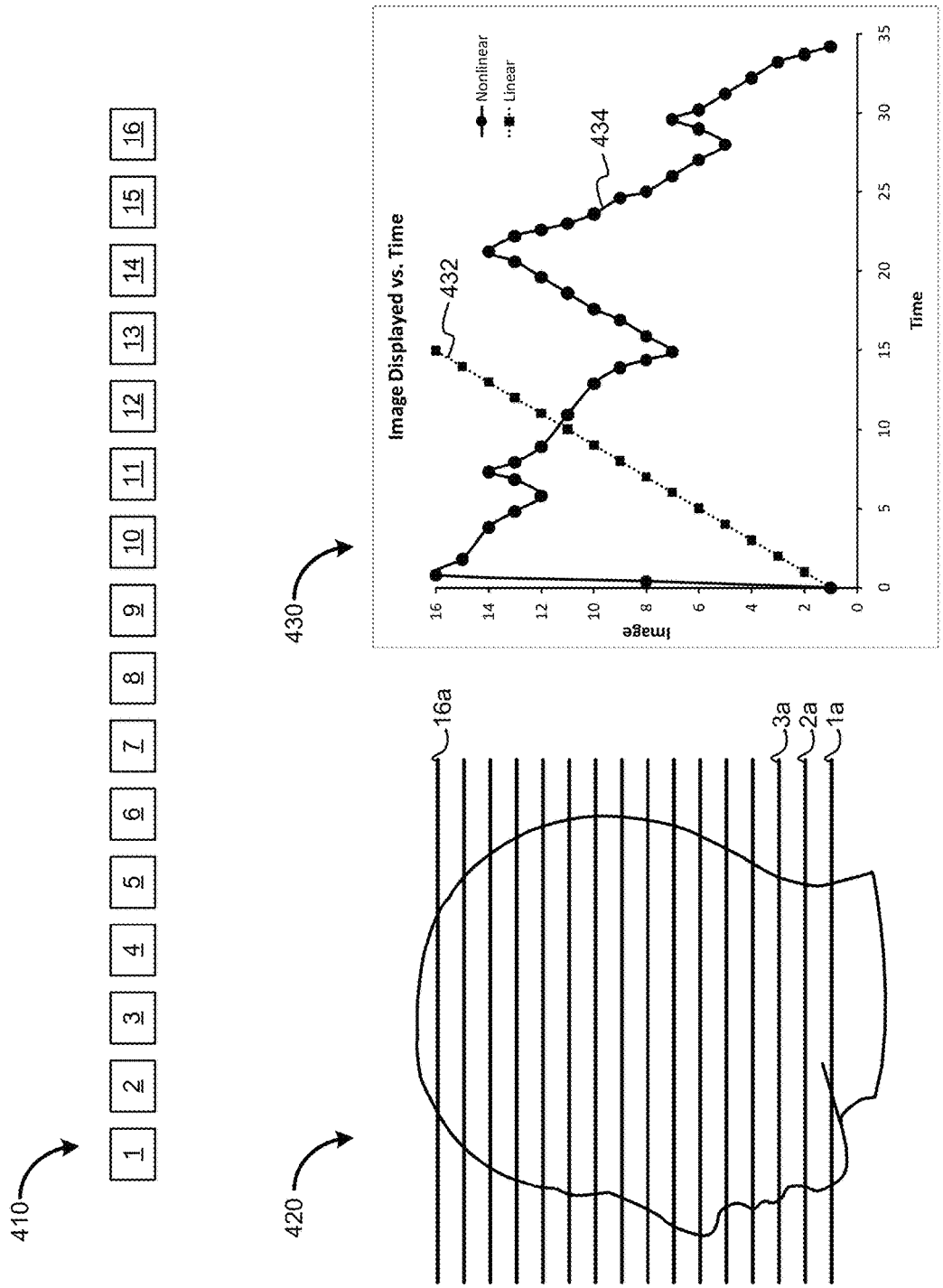
FIG. 4 includes a diagram illustrating a head outline where the horizontal lines depict locations where cross sectional images may be obtained, and a graph showing how those images are displayed as a function of time.

Referring to FIG. 4, view 410 illustrates 16 images, for example video frames within a movie. In practice, these video frames may be viewed in a linear order, starting with the first image and progressing to the last image. Graph 430 shows image number displayed as a function of time. This linear order of image viewing within a movie (or other data set) is illustrated by the data plotted with the dotted line 432 in the graph 430. Since the data is consumed in a linear fashion it is possible for the computing device to efficiently preload images that follow the image being viewed. For example, if image 7 is the current image displayed, the system can accurately predict that image 8 will follow, followed by 9, 10, 11, etc. In contrast, doctors often view images within a medical exam, for example, in a nonlinear fashion, as illustrated by the solid line 434 in the graph 430.

Diagram 420 illustrates a head outline where the horizontal lines labeled 1a to 16a depict locations where cross sectional images may be obtained, for example utilizing computed tomography (CT) or magnetic resonance imaging (MRI). The data plotted with the solid line 434 in graph 430 depicts the nonlinear order that the images were displayed by a particular user, such as a doctor examining the images of the brain. In this example, the user viewed images in the following order, 1, 8, 16, 15, 14, etc. In contrast to the movie example, the images were not viewed consecutively from 1 to 16, and many images were viewed more than once. Accordingly, simply preloading images in a linear order, such as may be done with a video, would not be effective in this case. However, the viewing order of images is not random. For example, in the case of FIG. 4, the doctor generally moves from one image to an adjacent image. In addition, once moving in one direction, he tends to continue to move in that direction.

As discussed herein, a computing system may be configured to monitor behaviors of users associated with image viewing and collect image viewing behavior that may be used to predict which images a doctor is likely to view next. Such viewing behavior data may be used to prioritize transfer and/or processing of images (either in a current exam or in other later accessed exams) to increase system responsiveness and therefore physician efficiency. In various embodiments, information used to predict which images are going to be needed next, e.g., by selecting a processing model that is usable to determine the predicted processing order, may be based on one or more of the following:

- Display data that indicates user behaviors in displaying images, for example, based on tracking of images that are displayed to the user.
- Characteristic data that indicates characteristics of the displayed information or other information associated with the displayed information. For example, in the case of medical imaging exams, the characteristic data might include modality, clinical information, user role, type of physician, etc. associated with a series of medical images.
- Behavior data (also referred to as viewing behavior data or user behavior data, may include, for example, display data and/or characteristic data, as well as results of analysis of such data, such as models usable to predict next images that will be requested for display) of a single user or multiple users.
- User, user group, system, default, or other rules.

To illustrate implementation of these features, medical imaging information will be discussed. However, systems and methods described herein may be used for other types of image data as well as non-imaging digital information stored in a computing device's memory. These methods could be used in a wide range of computing devices including personal computers, PDA's, and smartphones. Certain methods are described herein with reference to preloading of images from remote image storage into a memory buffer or other local memory. However, the described methods may also be used in order to optimize other processing tasks, such as decompression of images, image processing (e.g., computer aided diagnosis (CAD) analysis), image construction (multiplanar reconstruction (MPR), maximum intensity projection (MIP) or 3D volume rendering), and/or any other process.

Example Computing Systems

FIG. 1 is a system diagram that shows the various components of a system 100 for displaying information utilizing certain systems and methods described herein. As shown, the system 100 may include an information display computing device 150 (also referred to herein as a "computing device 150") and may include other systems, including those shown in FIG. 1.

The computing device 150 may take various forms. In one embodiment, the computing device 150 may be a computer workstation having modules 151. In other embodiments, modules 151 may reside on another computing device, such as a web server, and the user directly interacts with a second computing device that is connected to the web server via a computer network. The modules 151 will be described in detail below.

In one embodiment, the computing device 150 comprises a server, a desktop computer, a workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 150 may run an off-the-shelf operating system 154 such as a Windows, Linux, MacOS, Android, or iOS. The computing device 150 may also run a more specialized operating system which may be designed for the specific tasks performed by the computing device 150.

The computing device 150 may include one or more computing processors 152. The computer processors 152 may include central processing units (CPUs), and may further include dedicated processors such as graphics processor chips, or other specialized processors. The processors generally are used to execute computer instructions based on the modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Lua, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The computing device 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The computing device 150 may also include one or more interfaces 157 which allow information exchange between computing device 150 and other computers and input/output devices using systems such as Ethernet, Wi-Fi, Bluetooth, as well as other wired and wireless data communications techniques.

The modules of the computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing device 150 may be combined into fewer components and modules or further separated into additional components and modules.

The computing device 150 may communicate and/or interface with other systems and/or devices. In one or more embodiments, the computing device 150 may be connected to a computer network 190. The computer network 190 may take various forms. It may be a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanners 120. The MRI scanner 120 may be used to acquire MRI images from patients, and may share the acquired images with other devices on the network 190. The network 190 may also include one or more CT scanners 122. The CT scanners 122 may also be used to acquire images and, like the MRI scanner 120, may then store those images and/or share those images with other devices via the network 190. Any other scanner or device capable of inputting or generating information that can be displayed as images or text could be included, including ultrasound, angiography, nuclear medicine, radiography, endoscopy, pathology, dermatology, etc.

Also connected to the network 190 may be a Picture Archiving and Communications System (PACS) 136 and PACS workstation 138.

Also connected to the network 190 may be an image viewing behavior data structure 160. The image viewing behavior data structure 160 is a database or other data structure used to store information in certain embodiments described herein. In various embodiments, the Image Viewing Behavior Data Structure may reside within PACS System 136, reside within a server accessible on a LAN that is local to the computing device 150, and/or reside within a server that is located remote to the computing device 150 and/or accessible via the Internet. In other embodiments, image viewing behavior data structure 160 may reside locally, within computing device 150. Information may be stored in the image viewing behavior data structure 160 (and/or elsewhere) and may be stored in any computer readable format such as a database, flat file, table, or XML file, and may be stored on any computer readable medium, such as volatile or non-volatile memory, compact disc, digital video disc, flash drive, or any other tangible medium.

The PACS System 136 is typically used for the storage, retrieval, distribution and presentation of images (such as those created and/or generated by the MRI scanner 120 and CT Scanner 122). The medical images may be stored in an independent format, an open source format, or some other proprietary format. One common format for image storage in the PACS system is the Digital Imaging and Communications in Medicine (DICOM) format. The stored images may be transmitted digitally via the PACS system, often reducing or eliminating the need for manually creating, filing, or transporting film jackets.

The network 190 may also be connected to a Radiology Information System (RIS) 140. The radiology information system 140 is typically a computerized data storage system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a Laboratory Information System 144. Laboratory Information System 144 is typically a software system which stores information created or generated by clinical laboratories. Also attached to the network 190 may be a Digital Pathology System 146 used to digitally manage and store information related to medical pathology.

Also attached to the network 190 may be a Computer Aided Diagnosis System (CAD) 148 used to analyze images. In one embodiment, the CAD 148 functionality may reside in a computing device separate from computing device 150 while in another embodiment the CAD 148 functionality may reside within computing device 150.

Also attached to the network 190 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from computing device 150 while in another embodiment the 3D Processing functionality may reside within computing device 150.

In other embodiments, other computing devices that store, provide, acquire, and/or otherwise manipulate medical data may also be coupled to the network 190 and may be in communication with one or more of the devices illustrated in FIG. 1, such as with the computing device 150.

As will be discussed in detail below, the computing device 150 may be configured to interface with various networked computing devices in order to provide efficient and useful review of medical examination data that is stored among the various systems present in the network. In other embodiments, computing device 150 may be used to display non-medical information.

Depending on the embodiment, the other devices illustrated in FIG. 1 may include some or all of the same components discussed above with reference to the Information Display Computer Device 150.

Figure 2:
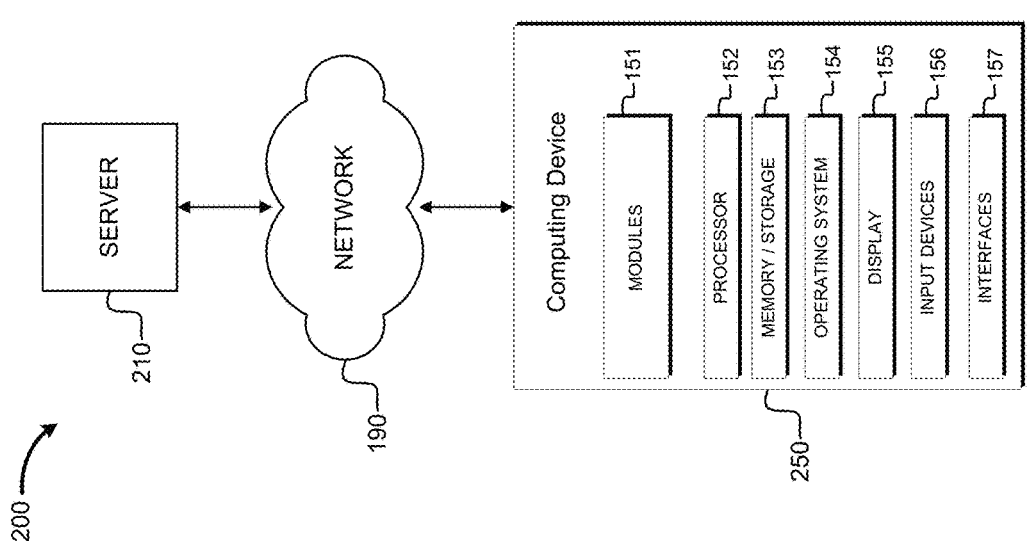
FIG. 2 is a system diagram which shows the various components of a system for managing data (e.g., medical or non-medical data) utilizing certain systems and methods described herein.

FIG. 2 is a system diagram which shows the various components of a system 200 for managing data (e.g., medical or non-medical data) utilizing certain systems and methods described herein. As shown, the system 200 may include a computing device 250 and may include other systems, including those shown in FIG. 2.

The computing device 250 may take various forms. In one embodiment, the computing device 250 may be a computer workstation having modules 151. In other embodiments, modules 151 may reside on another computing device, such as a web server, and the user directly interacts with a second computing device that is connected to the web server via a computer network. The modules 151 are described above with reference to FIG. 1.

In one embodiment, the computing device 250 comprises a server, a desktop computer, a workstation, a laptop computer, a mobile computer, a Smartphone, a tablet computer (e.g., the tablet computer 320 of FIG. 3), a cell phone (e.g., the smartphone 330 of FIG. 3), a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 250 may run an off-the-shelf operating system 154 such as a Windows, Linux, MacOS, Android, or iOS. The Information Display computing device 250 may also run a more specialized operating system which may be designed for the specific tasks performed by the computing device 250.

As with Information Computing Device 150 described herein with reference to FIG. 1, computing device 250 may include one or more computing processors 152, may include memory storage 153, may include or be interfaced to one or more display devices 155, may include or be interfaced to one or more input devices 156, may include one or more interfaces 157.

The computing device 250 may communicate and/or interface with other systems and/or devices via network 190, as described herein with reference to FIG. 1.

In the embodiment of FIG. 2, a Server 210 is connected to the network 190 and configured to communicate with the computing device 250, for example allowing communication of images or other data between Server 210 and computing device 250.

In various embodiments, the image viewing behavior data structure 160 (FIG. 1) may be stored in Server 210, computing device 250, or in another computing system in communication with Server 210 and/or computing device 250.

Figure 3:
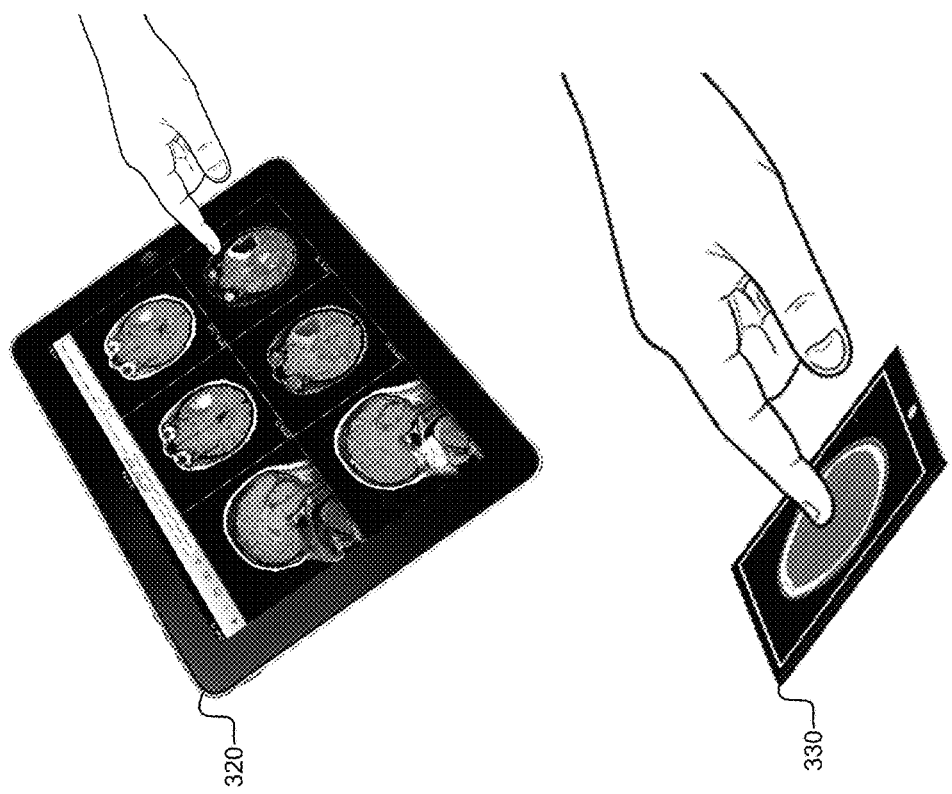
FIG. 3 illustrates an example tablet computer and smartphone.

FIG. 3 illustrates example computing systems that may be used in embodiments described herein, such as the tablet computer 320 and smartphone 330. For example, the computing device 150 or 250 could include the smartphone or tablet computer illustrated in FIG. 3. As discussed above, the system and methods described herein may be implemented on any other suitable computing device, such as those listed above.

Example Methods

Figure 5B:
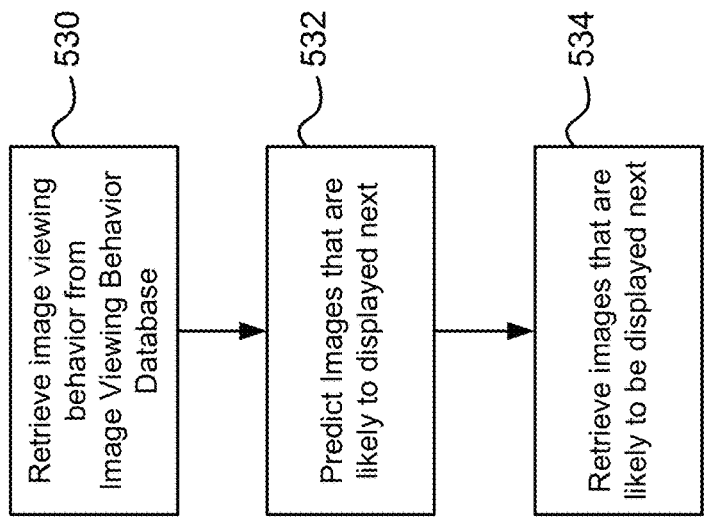
FIG. 5a and FIG. 5b are flowcharts that provide a high level overview of certain methods that may be performed, for example, in order to determine behavior data associated with a user and then to use that behavior data to customize presentation of data to the user.
Figure 5A:
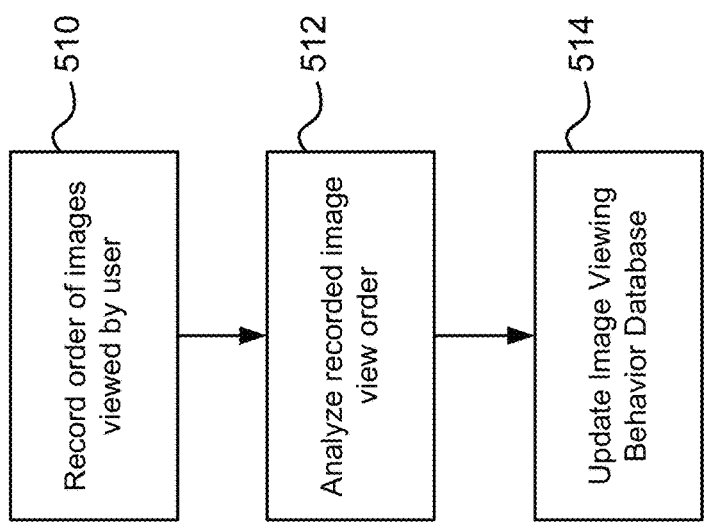

FIG. 5a and FIG. 5b are flowcharts that provide a high level overview of certain methods that may be performed by the computing device 150 or 250, for example, in order to determine behavior data associated with a user and then to use that behavior data to customize presentation of data to the user. Depending on the embodiment, the method of FIGS. 5a and 5b may include fewer or additional blocks and/or the blocks may be performed in an order different than illustrated.

Medical imaging exams typically comprise one or more "series", where each series includes one or more images that share a common characteristic, e.g., contrast weighting in MRI, plane of acquisition, reconstruction algorithm in CT, whether the images where obtained before or after intravenous contrast administration, etc. Images within a series may differ on one or more characteristics, such as spatial position, projection, or acquisition time.

For example, a brain MRI might include the following series: sagittal T1, axial T1, axial FLAIR, axial T2, axial diffusion, coronal gradient echo, post-contrast axial T1, post-contrast coronal T1, and post-contrast sagittal T1 weight images. In the example of a brain MRI exam, each series would typically include a group of images at different spatial positions. In the example of an axial T1 series of the brain, image number 1 might be acquired at the inferior aspect of the brain, with image number 2 acquired 2 mm superior to the position image 1, image 3 acquired 2 mm superior to the position of image 2, and so on.

Computing devices used to present images from medical imaging exams typically display one or more image frames on a computer display, where each image frame may be allocated to a series and one image of the series is displayed within the corresponding image frame. For example, a series might include 100 images, numbered 1 to 100, with image number 49 displayed in the image frame for that series.

In response to user input, other images from the series may be displayed within the image frame. For example, pressing a particular key on a computer keyboard might increment the number of the image displayed (e.g., to image number 50 in the example above) while pressing another key might decrement the number of the image displayed (e.g., to image number 48 in the example above). Alternatively, pressing the left mouse button and moving the mouse up might increment the image number while moving the mouse down might decrease the image number. Alternatively, different gestures on a touch sensitive device (e.g., a touchscreen), such as up and down swipes, might indicate instructions to increment or decrement the number of the image displayed. Using these or other forms of user input allows the user to navigate through the various images within a series.

In some cases, more than one series may be displayed simultaneously (e.g., in different image frames) and changing the image displayed in one series may automatically result in changing the image displayed in another series Linking the display of images in various series may be advantageous as it may improve user efficiency, for example when a user is comparing images from different series.

FIG. 5a is a flowchart that shows one embodiment of a method of collecting, analyzing and storing behavior data indicating a user's image display behavior. Depending on the embodiment, the method of FIG. 5a may include additional or fewer blocks and/or the blocks may be performed in an order different than is illustrated.

In block 510, the computing device (e.g., computing device 150 or 250) receives an indication of the user utilizing the computing device, monitors the user's interactions, and records the order in which the user views images in one or more medical imaging exams in viewing behavior data. In various embodiments, additional information may be collected and stored in the viewing behavior data, which may be used to stratify image viewing behavior based on a number of factors, such as, for example:

Modality, e.g., MRI, CT, etc.
Exam type, e.g., MRI of brain, MRI of spine, etc.
Clinical indication for the exam.
The patient's clinical history.
The region of the body being viewed.
Direction of scanning used to acquire the images (e.g., movement towards the top of the patient or movement towards the bottom of the patient)
Aspects of the images being displayed, e.g.,
  Technical parameters related to the images, e.g.,
    Series type, e.g. for MRI, T1, T2, FLAIR, etc.

Series description
2D or volumetric acquisition
Slice thickness
Resolution
Image size
Image type, e.g.,
  Primary acquisition
  MPR (multiplanar reconstruction)
  MIP (maximum intensity projection)
  3D volume rendering
Whether images were obtained with or without intravenous contrast administration
Associations with comparison exams, for example image viewing behavior related to how brain MRI images from a prior exam are displayed in relation to images from a current brain MRI.
Type of display device, e.g., PC, tablet, smartphone, etc.
The number and/or size of the display devices associated with the computing device
The amount of memory in the computing device
The speed of transmission between the computing device and other connected devices, e.g., a remote image storage device.

In block 512, the viewing behavior data of one or more users may be analyzed, for example to allow prediction of the next images that are most likely to be viewed, for example as discussed with reference to FIG. 6*a*. For example, the viewing behavior data may be processed in order to generate a processing model that is predictive of viewing orders for other similar image series (e.g., image series of the same modality that are requested by the same doctor).

In block 514, the viewing behavior data structure (e.g., database) is updated with the results of the analysis, such as in the form of a processing model that may be used to determine an order of transfer or display of images.

FIG. 5*b* is a flowchart that shows one embodiment of a method of utilizing stored viewing behavior data, which may include analysis of the viewing behavior data, such as in the form of a model or other data structure, to prioritize the communication and/or processing of images that the user is likely to view next.

In block 530, the previously stored processing model (which may also be referred to as a viewing behavior model in an embodiment where viewing behavior is being predicted by the processing model) is accessed, such as by requesting and receiving the model from the image viewing behavior data structure 160. In various embodiments, other information may be retrieved that may be used to associate information in the image viewing behavior data structure with a particular user or aspects of the exam or exams being viewed by the user, such as the factors discussed above with respect to block 510.

In block 532, a computing device predicts the image or images that the user is likely to view next based on the accessed viewing behavior data, such as the viewing behavior model and/or other related data. The prediction may further be based on the user, the current image or images being displayed, and/or other factors, such as those discussed in reference to block 510 above.

In block 534, the images predicted to be displayed next are communicated to the computing device, such as to a local memory of the computing device. In other embodiments, one or more alternate or additional operations related to the image, or images, predicted to be needed next are preformed, such as image processing operations, decompression, etc.

Figure 6A:
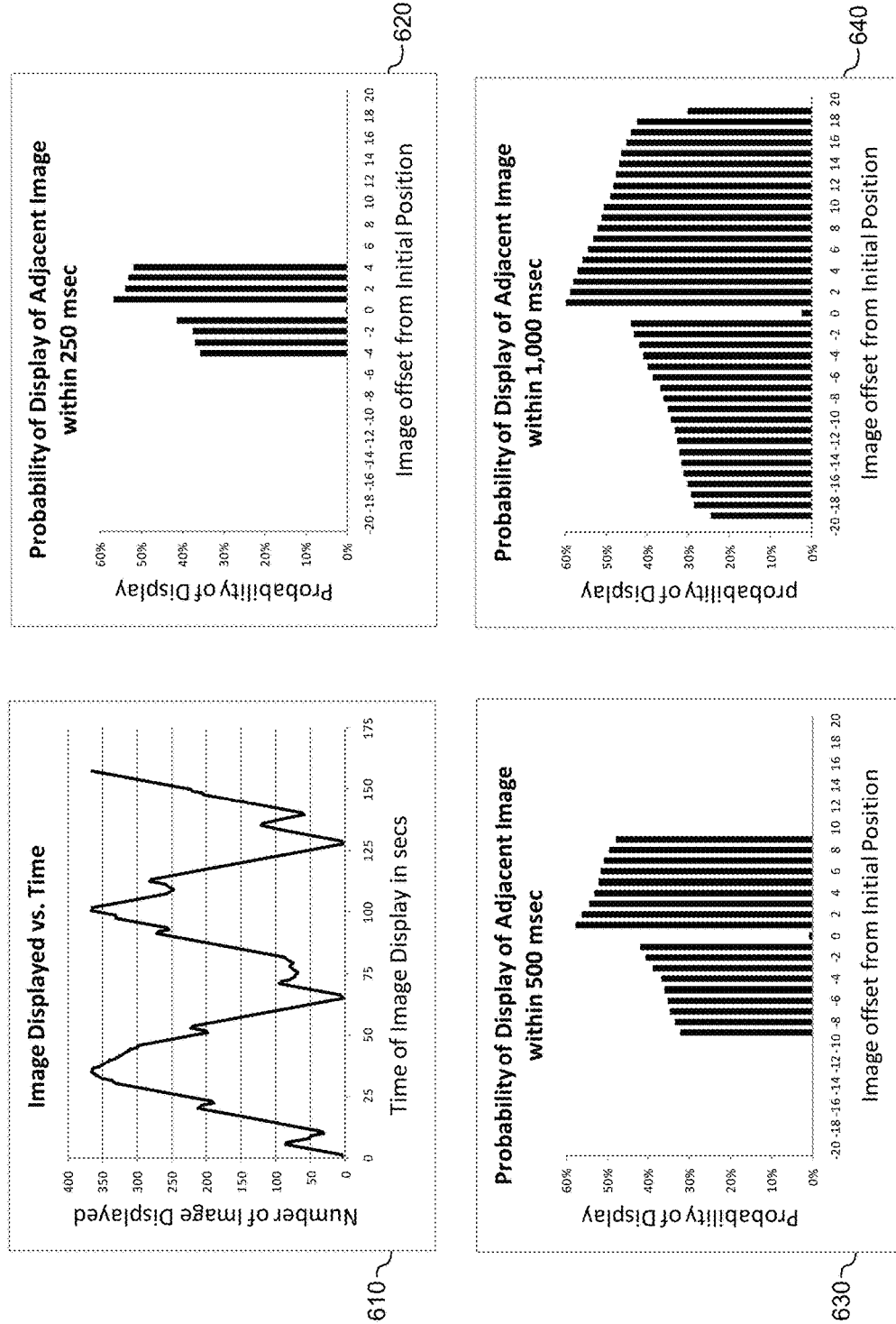
FIG. 6a includes a graph plotting images displayed as a function of time and three graphs illustrating sample probability data that is based on an analysis of the data of the first graph.

Sample Image Viewing Behavior and Associated Probabilities of Adjacent Image Display Graph 610 in FIG. 6*a* plots images displayed as a function of time as an example doctor views an example series of images. In this embodiment, sequential axial images within the series of the medical imaging exam are numbered, in this case from 1 to 360, and are indicated on the y-axis. The x-axis plots time in seconds during the course of the doctor viewing the images.

During the course of viewing the images in the exam the user is free to navigate through the various images any way he sees fit. He may move forward through the images, moving to higher numbered images, or move backwards through the images, moving to lower numbered images. Depending on the complexity of the anatomy (and/or other factors), users may view images more than once as they examine the different anatomic structures within the images and/or to view images with different display parameters. For example, the user behavior plotted in graph 610 indicates that the user moved forward through the images in the first 30 seconds or so, then backwards through the images in the next 30 seconds or so, followed by another review forward, backward, and then forward again. In addition to the general scrolling up and down through the images, graph 610 also shows some smaller reversals of order to review images of the series. For example, when the user first reaches about image 80 in the first few seconds of viewing, direction is changed and images 80 through 40 (about) are displayed again, before reversing direction and incrementing image numbers until about image 210.

By analyzing the viewing behavior depicted in graph 610, it is possible to determine the probability that the user will display an adjacent images and/or images at specific adjacency offsets from the current image. For example, graphs 620, 630, and 640 depict sample probability data that is based on an analysis of the data of graph 610.

Graph 620 plots the probability that images at different adjacency offsets from the current image will be displayed within the next 250 msec. For example, with any particular image in the image series displayed, there is an approximately 55% probability that the next consecutive image (adjacency offset=1) will be displayed and an approximately 41% probability that the prior image (adjacency offset=−1) will be displayed within the following 250 msec timeframe. There is a small probability (e.g., less than 1%) that the user will leave the particular image (adjacency offset=0) and return to it during the 250 msec timeframe. Graph 630 and Graph 640 depict analyses similar to the one show in Graph 620, but illustrate the probability of image display for timeframes of 500 msec and 1,000 msec respectively.

Figure 6B:
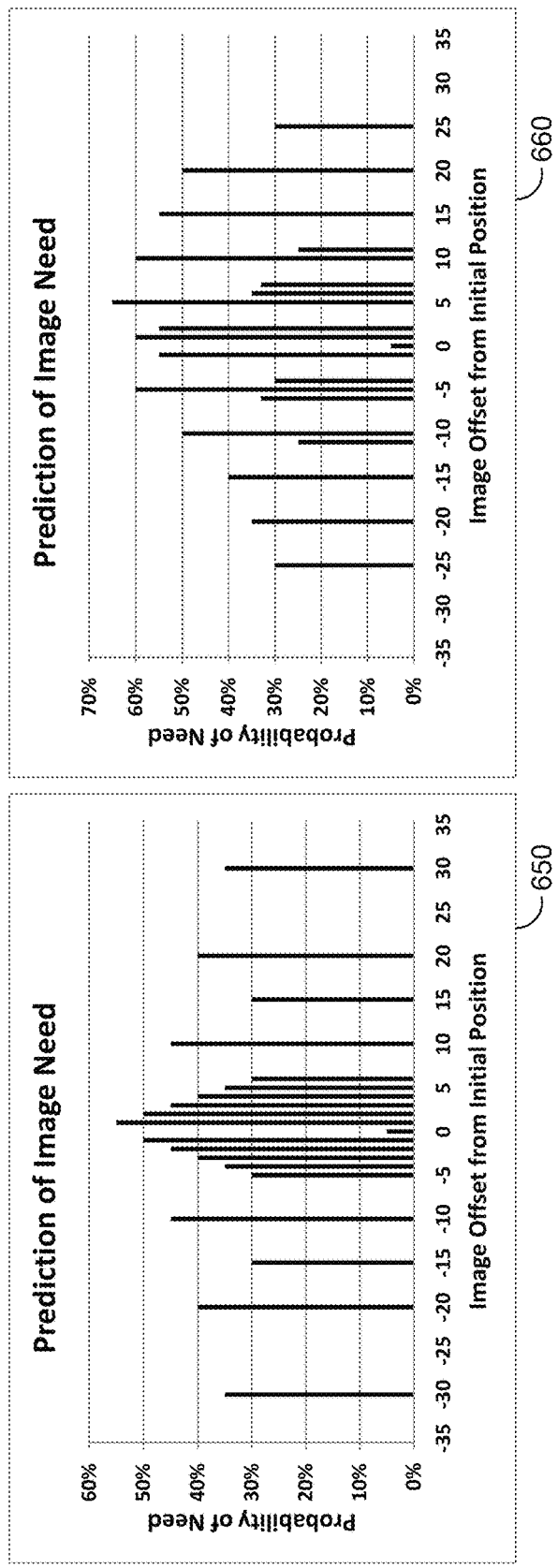
FIG. 6b illustrates probability data associated with different user behavior data.

In the user image viewing behavior depicted in graph 610 and analyzed data displayed in graphs 620, 630, and 640, the user navigated to adjacent images, without skipping images when navigating from one image to another. In other embodiments, image viewing behavior may include non-contiguous selection of images, e.g., moving from a current image to another image having an adjacency offset of more than 1. Example embodiments where preloading models include skipping adjacent images are depicted in graphs 650 and 660 of FIG. 6*b*. As shown in graph 650, the viewing behavior indicates relatively high probabilities that the user will select an image that is 5, 10, 15, 20, or 30 images away from a current image, without selecting images between images 5-10, 10-15, 15-20, or 20-30 images.

Example Image Preloading

FIGS. 7*a* and 7*b* are block diagrams illustrating example transfers of images from a remote image storage 710 to a memory buffer 730 (or other local memory) in accordance with viewing behavior of a user. In this embodiment, computer display 750 and input device 751 are part of a computing device, such as computing device 150 or 250, as described herein.

Memory buffer 730 may provide storage for one or more images, with seven in the example shown. In one embodiment, the computing system has access to memory buffer 730, allowing rapid display of one or more images on display 750. In various embodiments, memory buffer 730 is local to the computing device, such as a RAM, FLASH memory, disk drive memory, or other media or technology capable of storing digital data.

The computing device is in communication with image storage 710, which stores one or more images. In one embodiment, image storage 710 may be a component of a PACS system, e.g. PACS system 136 in FIG. 1. In another embodiment, image storage 710 may be a component of a server, such as server 210 in FIG. 2.

In the embodiments of FIG. 7a and FIG. 7b images may be communicated from image storage 710 to memory buffer 730. Communication of images is illustrated as arrows, such as arrow 770, via network 777. The network 777 may include any one or more of a variety of networks and communication technologies, such as those discussed with reference to the network 190 of FIG. 1.

In other embodiments, the communication of images from image storage 710 to memory buffer 730 may include a processing operation, such as image decompression.

In another embodiment the image storage 710 and memory buffer 730 are both local to the computing device. Rather than image communication from a remote to local computing device, systems and methods described herein may be utilized to manage image processing, such as image decompression, computer aided diagnosis (CAD) analysis, or 3D processing such as multiplanar reconstruction (MPR), maximum intensity projection (MIP) or 3D volume rendering.

In operation the user may provide input to the computing device, for example using input device 751, indicating an image to be displayed. In the example shown, the image to be displayed is image 722A, which is stored in the buffer 730 and displayed on image display 750, illustrated by arrow 775.

In the embodiment of FIG. 7a, images are retrieved from the image store 710 in a nonlinear order, according to the viewing behavior data of the particular user, such as data that is compiled in response to monitoring behavior of the user while interacting with one or more previous similar exams. In this particular example, the images in the buffer don't simply include a quantity of images immediately before and after the currently viewed image; rather, the image buffer 730 includes images that are most likely to be viewed next by the particular doctor (e.g., based on a processing model generated through analysis of viewing behavior data of the user). In this example, images 720 and 726 are not loaded into the memory buffer 730, while images that are further from the currently displayed image (e.g., image 719 and image 727) are copied to the memory buffer 730.

In a similar manner, the images retrieved from the image store 710 in FIG. 7b are also nonlinear. In this embodiment, the currently viewed image 722a is stored in the buffer 730, along with the immediately adjacent images 721a and 723a. However, the next adjacent images (720 and 724) are not currently loaded in the image buffer 730. As discussed above, the particular images that are loaded into the buffer 730 (and/or otherwise decompressed, modified, or processed for viewing) at any point in time may be determined based on viewing preferences of the user and associated predictions of the images that the user will view next.

FIG. 7c illustrates an embodiment wherein image data is stored in a compressed format in local storage 760 (could also be remote storage in other embodiments) and is decompressed and stored in memory 730 in an order determined by the viewing behavior data of the user, such that the images that are most likely to be displayed next are decompressed prior to need for the decompressed images. In this embodiment, images 712c-729c (where the "c" indicates that images are compressed) are selected according to a processing model (e.g., that is developed based on viewing behavior data) and stored in memory buffer 730 in a decompressed format that is more quickly available for display on the display device 750. In FIG. 7c, decompressed images 717d, 719d, 721d, 722d, 723d, 725d, and 727d (where the "d" indicates that the images are decompressed) are illustrated as being stored in memory buffer 730. The content of the memory buffer 730 may be updated dynamically based on changes in the displayed medical images by the user and the processing model selected for determining which images of the image series to decompress next, for example. As noted herein, any other processing may be coordinated based on a processing model.

Figure 7D:
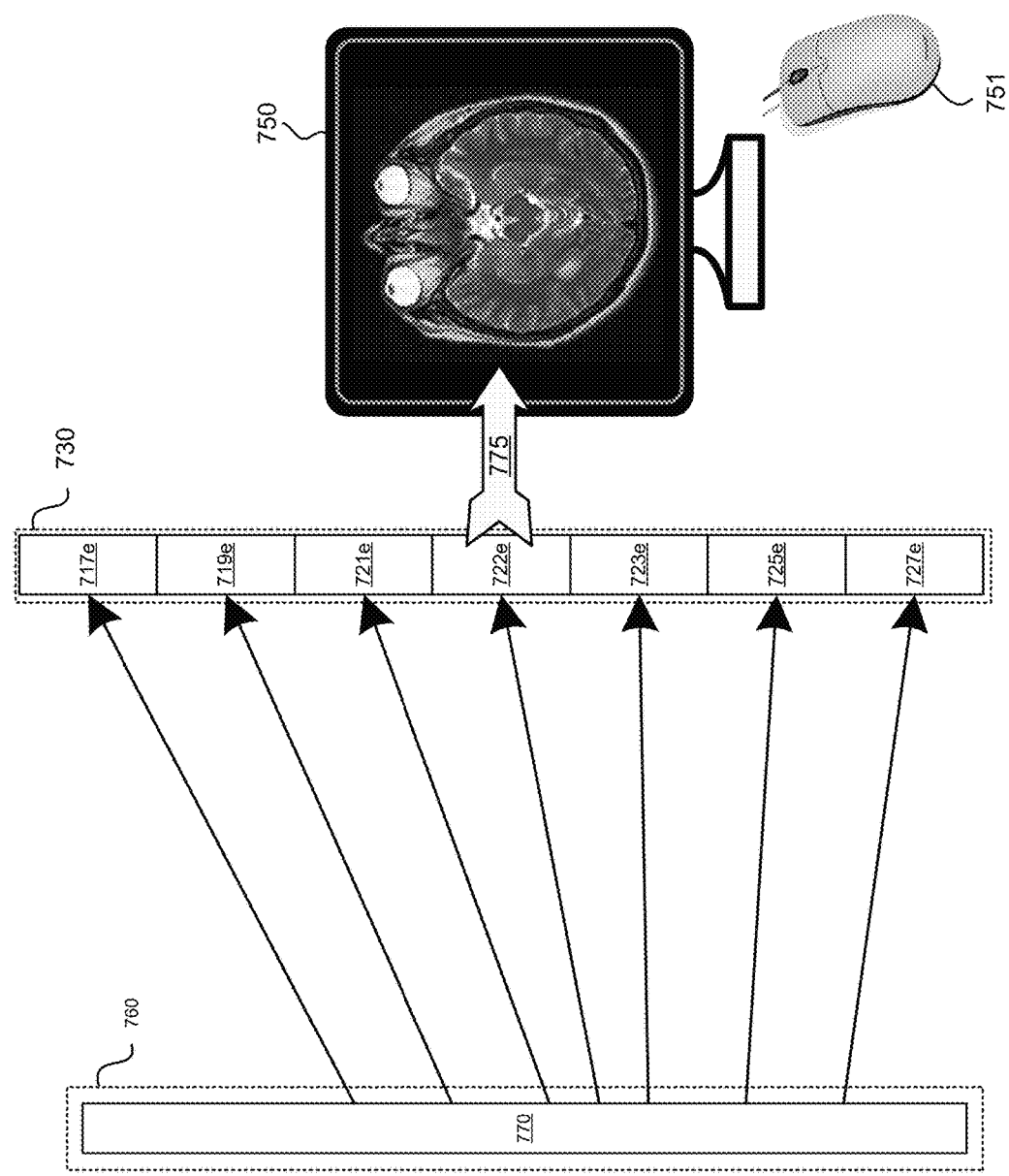
FIG. 7d is a block diagram illustrating an example construction of images from an imaging volume in accordance with a processing model.

FIG. 7d illustrates an embodiment wherein image data comprises an imaging volume, such as a 2-D or 3-D imaging volume, is used to construct images for display on the display device 750 in an order that is determined by a selected processing model. In this particular example, imaging volume 770 may be stored in a local storage 760 or a remote storage that is accessible via one or more networks. Depending on the embodiment, the image construction process may be performed by a device that is local to the memory buffer 730 or by some other device, such as a network connected image reconstruction server. In either case, the images to be constructed from the imaging volume 770 are determined based on viewing behavior data of the user such that the images that are most likely to be accessed next by the user are already constructed when the user requests those images. In this embodiment, images 717e, 719e, 721e, 722e, 723e, 725e, and 727e are constructed and stored in the memory buffer 730.

Example Methods

Figure 8:
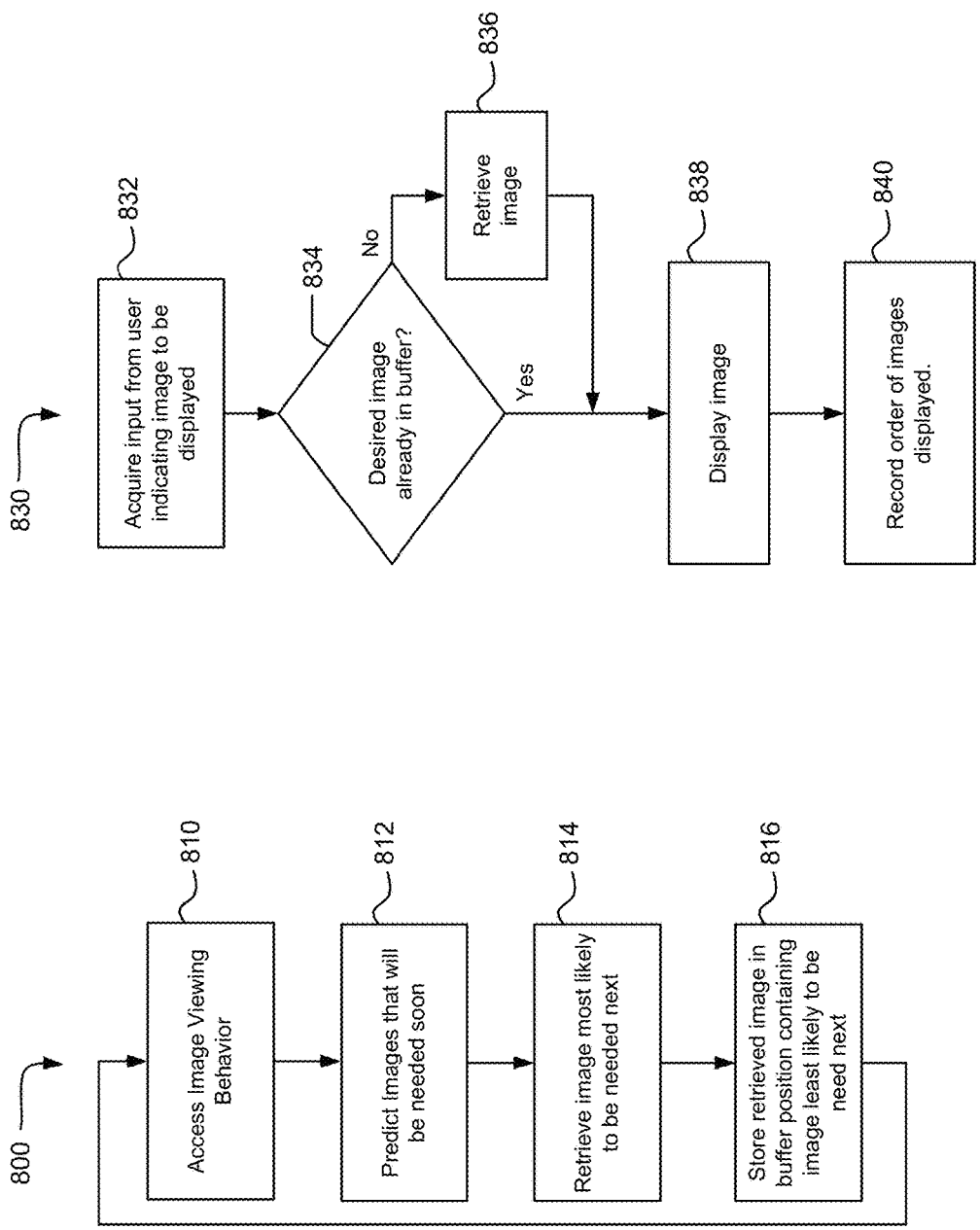
FIG. 8 is a flowchart illustrating embodiments of methods that may be utilized in conjunction with the computing devices described in FIG. 7a-7d, for example.

FIG. 8 is a flowchart illustrating embodiments of methods that may be utilized in conjunction with the computing devices described in FIGS. 7a-7d, for example. The method in flowchart 800 may occur in parallel or in series with respect to the method of flowchart 830.

Flowchart 800 illustrates an example process for preloading of images, for example from image storage 710, into memory, such as memory buffer 730 (FIGS. 7a and 7b). The methods of FIG. 8 may be performed, for example, by the computing system 150 or 250, or any other suitable computing system.

In block 810, the image viewing behavior (e.g., imaging viewing models and/or other information developed in analyzing the image viewing behavior) is accessed, for example from image viewing behavior data structure 160.

In block 812, a prediction is made of the images that are likely to be displayed next by the user based on the imaging viewing behavior. If one or more images are being displayed, this prediction may also be based on the image(s) being displayed.

In block 814, the image or images most likely to be needed next are retrieved or otherwise communicated, for example from image storage 710.

In block 816, the retrieved image or images are stored in a local storage device, such as an image buffer, for example memory buffer 730. In one embodiment, if the images slots in the memory buffer are already filled, the newly retrieved images are placed in the slots that contain images that are least likely to be viewed next, such as may be determined using the image viewing behavior.

The above methods illustrate logic associated with communication and preloading of images from remote image storage into a memory buffer. However, in other embodiments, similar logic could be used to perform other operations such as decompression or image processing.

Flowchart 830 illustrates steps related to displaying images in response to user input, in one embodiment.

Beginning in block 832, input is acquired from the user that indicates the image or images that the user would like to display, for example using input device 751. In various embodiments, user input could utilize a mouse, trackball, touchpad, touchscreen, keyboard, voice commands, and/or other forms of input.

In block 834, the computing device determines whether the desired image is already in the image buffer, such as memory buffer 730. If the desired image is in the buffer, the method proceeds to block 838. If the desired image is not in the buffer, the method proceeds to block 836.

In block 836, an image needed for display is retrieved. In one embodiment, the retrieved image is stored in the memory buffer. In another embodiment, the retrieved image is displayed but not stored in the memory buffer.

In block 838, the image is displayed.

In block 840, an optional step, an order of the images displayed is recorded, for example as described in reference to block 510 of FIG. 5. This may be used to create or refine the user behavior data, such as the models used to predict next images.

Multiple Series

Figure 9A:
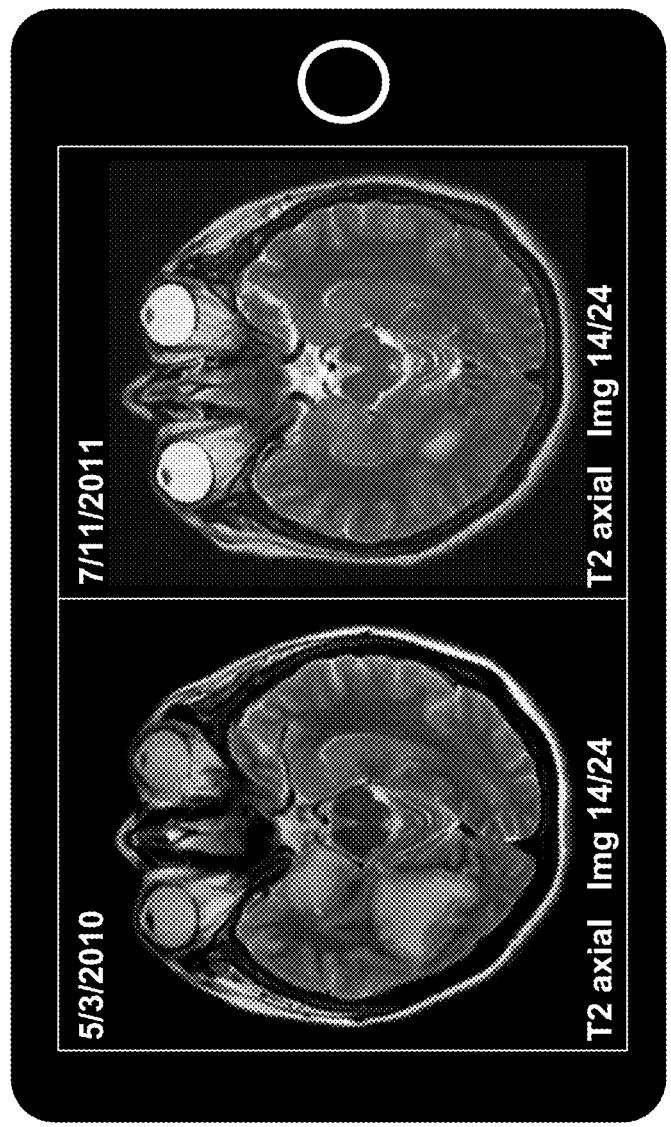
FIG. 9a depicts a computing device, in this example a smartphone, displaying two image frames, each with a different series.

FIG. 9a depicts a computing device, in this example a smartphone, displaying two image frames, each with a different series. In the example shown, the frame on the left displays an image from a T2 weighted series from a brain MRI dated May 3, 2010 and the frame on the right displays an image from a T2 weighted series of the brain dated Jul. 11, 2011. The displayed images from each series display a similar anatomical position of the brain, allowing the user to assess changes that may have occurred in the timeframe between the scans.

As discussed above, the display of the series may be linked so that when the user changes the image displayed within a series in one frame, the image in the other frame is automatically changed. In the example shown, each of the two series has 24 images and image number 14 from each series is displayed. In this example, if the user were to increment the image displayed in the left image frame to 15 (e.g., by touching the left frame with his finger), then the linked series in the frame on the right would be automatically updated to display image 15 from the other series also.

Linked series may be from different exams, as illustrated in the example of FIG. 9a. Alternatively, linked series may be from the same exam. In addition, linked series may comprise series from the same and different exams. When linked series comprise series from different exams, the exams may be of the same or different types, for example different modalities.

The systems and methods described herein may be applied to linked series, where changing the image that is displayed in one series automatically results in changing the image displayed in a second series.

Figure 9B:
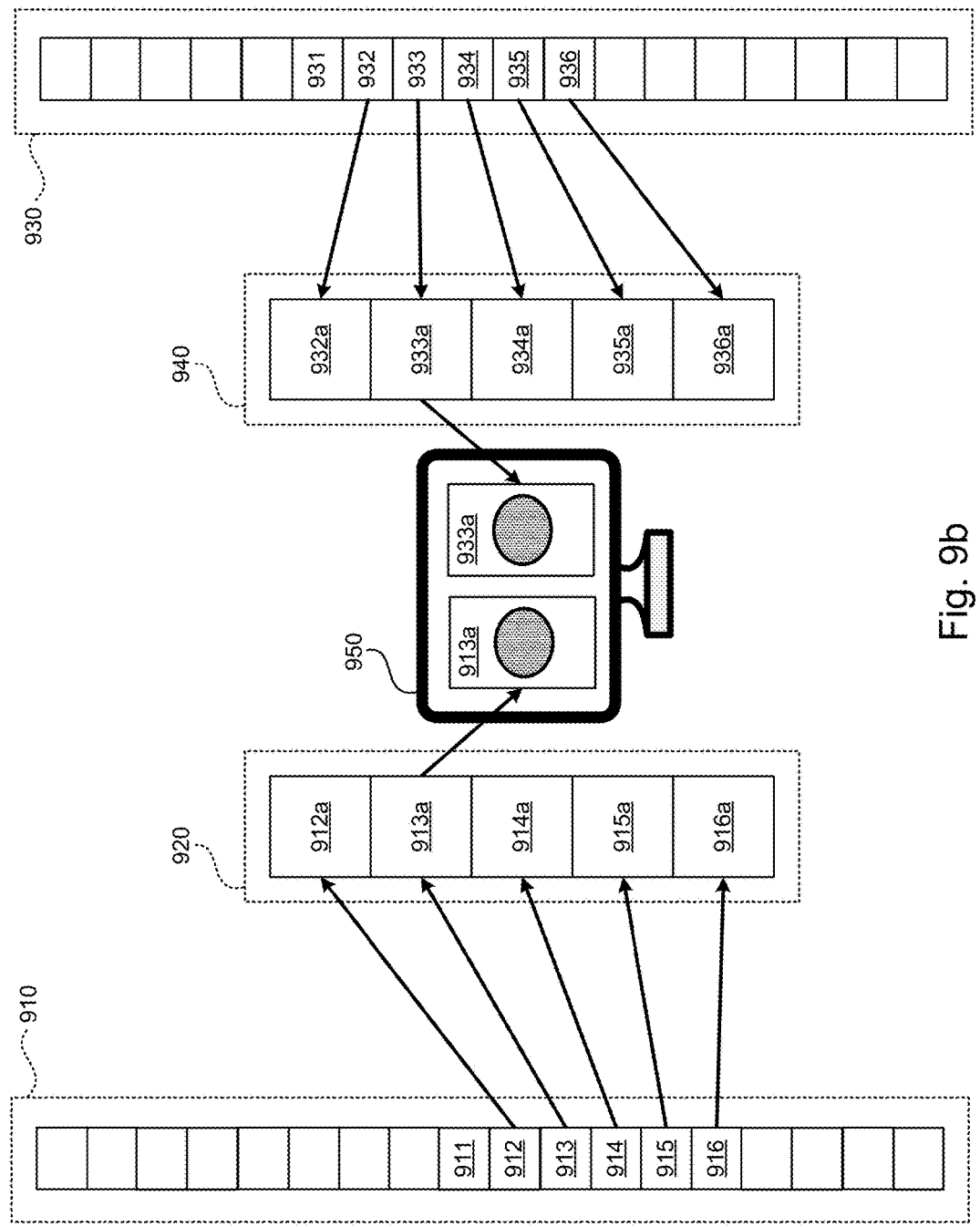

FIG. 9b is a block diagram illustrating preloading of images from linked image series, such as the image series including the images discussed with reference to FIG. 9a.

In one embodiment the preloading behavior models for the multiple displayed image series are applied independently. In other embodiments, a common preloading behavior model may be used on each linked series. As shown in FIG. 9b, images of a first series (that includes image 913a that is currently depicted on the display 950) are stored in a first remote storage system 910 and images of a second series (that includes image 933a) are stored in a second remote storage system 930. The first and second remote storage systems may be separate PACS servers, for example, or any other device of FIG. 1, for example. In other embodiments, the remote storage systems are a single system.

As illustrated in FIG. 9b, the images of the buffers 920 and 940 (e.g., one or more local storage devices) are filled with images in a same manner in view of the similar modality of the two image series. In particular, one image prior to the currently displayed image (e.g., images 912a and 932a) are buffered, as well as three images after the currently displayed image (e.g., images 914a-916a and 934a-036a). This preloading pattern may be based on previous viewing behavior of the particular user that is viewing the image series.

If another user accesses the same two image series, the preloaded images may differ, in accordance with different viewing behaviors of the user. For example, images that are non-adjacent to other pre-loaded images may be buffered in accordance with user viewing behavior, such as is illustrated in FIGS. 7a and 7b.

In one embodiment, the multiple image series may be preloaded using different preloading models. For example, if the two image series illustrated in FIG. 9b are of different modalities, images of the series may be preloaded in accordance with viewing behavior models associated with the respective modalities. In such an embodiment, the image series may or may not be linked.

Figure 10A:
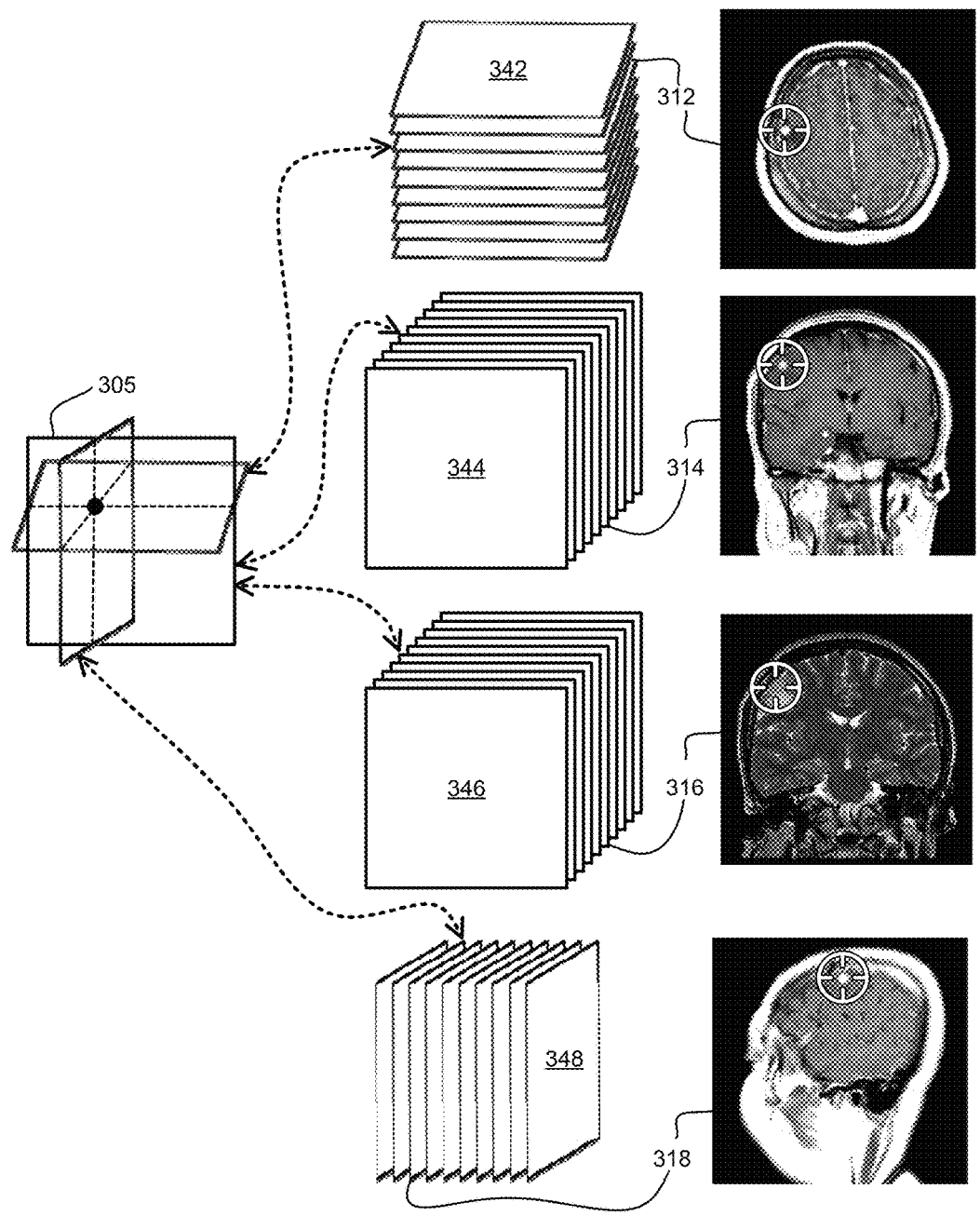
FIG. 10a illustrates display of images from different series of a medical imaging exam in response to movement of a 3D cursor.

FIG. 10a illustrates display of images from different series sharing a common frame of reference 305. The 3D cursor is depicted as a white circle with 4 lines extending inwardly superimposed on displayed images from the various example series 342, 344, 346 and 348. The position of the center of the 3D cursor represents the same 3D spatial position within each of the series, as will be discussed further with reference to FIG. 11. The user may move the 3D cursor within any series, for example by positioning a cursor over the 3D cursor, depressing a mouse button, and moving the mouse. In one embodiment, moving the 3D cursor within any image moves its 3D position within the 3D frame of reference 305, and the images displayed in the various planes and the position of the 3D cursor are changed to reflect the new position.

In the example of FIG. 10a, images from series acquired along three different planes are displayed including an axial plane 342, a coronal plane 344 and 346, and a sagittal plane 348. In other embodiments, images in different planes may be reconstructed from one or more 3D volumes, wherein the position of a plane of reconstruction is determined based on the position of the 3D cursor.

Various series within a medical imaging volume may comprise images of regions of a patient's body where the images within the various series comprise planes at different spatial positions. For example, an axial T1 series of the brain might consist of 200 images at 1 mm intervals, with each image 1 mm in thickness.

Various series within a medical imaging exam may image the region of interest in different or the same orientation and may be obtained with the same or different acquisition parameters.

In the example of FIG. 10a, the four series 342, 344, 346, 348 may be from a brain MRI wherein image 312 is an image from an axial T1 series 342, image 314 is an image from a coronal T1 series 344, image 316 is an image from a coronal T2 series 346, and image 318 is an image from a sagittal T1 series 348.

The position of the 3D cursor superimposed on each image corresponds to the 3D position of the black circle in 3D volume 305.

Figure 10B:
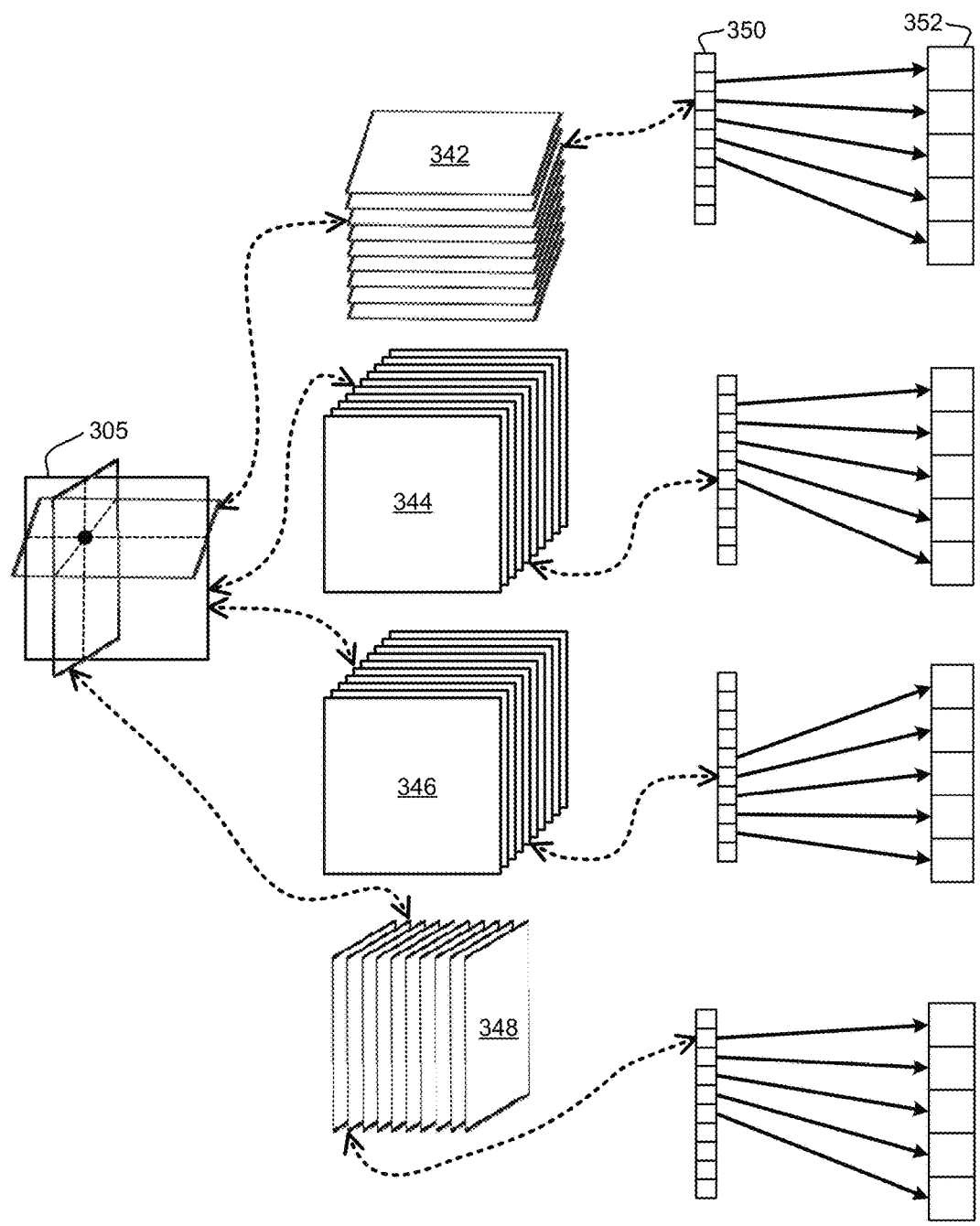
FIG. 10b illustrates preloading and/or processing of images around a location within multiple linked series.

FIG. 10b illustrates preloading and/or preprocessing of images around the position within each linked series. For example, preloading of different linked (or not linked) series may be performed simultaneously, based on the same or different preloading models.

In the example of FIG. 10b, series 342, 344, 346 and 348 represent different series in the same or different medical imaging exams that may be related to each other via the same or different 3D frame of reference 305, as in FIG. 10a. The images in each series may be selected for transfer to memory buffer(s) based on past and/or current viewing behavior associated with the viewing doctor. For example, images of the image series 342 that are stored in storage device 350 may be preloaded into memory buffer 352. Thus, the images selected for preloading may differ for each of the image series.

In one embodiment, imaging viewing behavior is tracked for individual image series 342, 344, 346, and 348 so that preloading of images from each series is performed with reference to previous viewing behaviors with reference to other image series with similar characteristics. Accordingly, the images that are preloaded for each image series may differ. For example, if a user typically moves through images in series of the same type as series 342 in increments of 5 images at a time, the images preloaded for that series may include images far away from the currently displayed image, such as 5, 10, and 15 images away. Similarly, if the user typically views images the same type as series 344 in a forward pattern (e.g., scrolls through the images in a forward pattern only once, without going backwards), images of series 344 that are preloaded may include only images that are ahead of the currently displayed image.

In one embodiment, local image storage may be allocated based on viewing behaviors. For example, if the images series 342 and 344 are concurrently displayed to a user, but the user very rarely navigates between images of series 344 and very frequently navigates between images of series 342, a larger portion of the image buffer may be allocated for storage of images from series 342.

Figure 11:
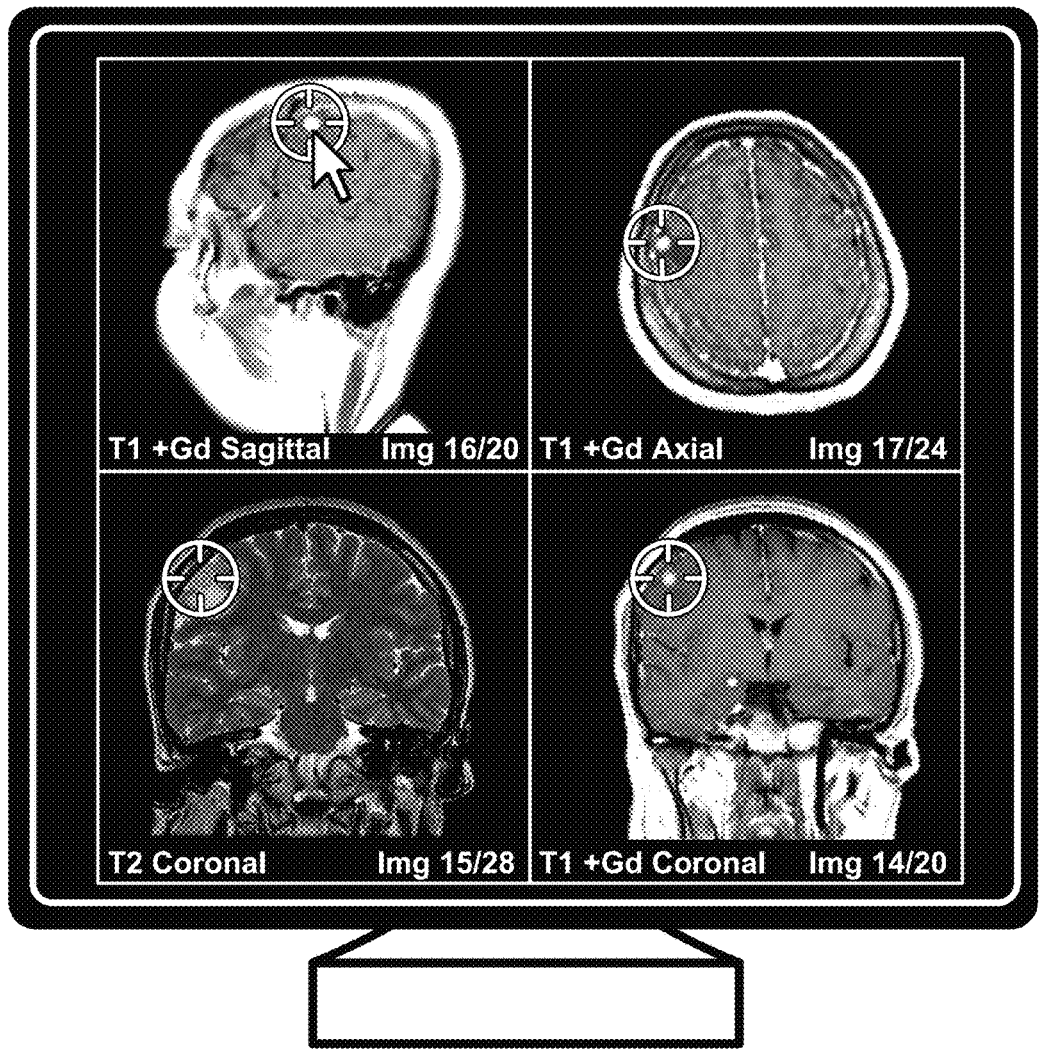
FIG. 11 illustrates an example computer display, in this case depicting four image display frames, each displaying an image from a different series and a 3D cursor.

FIG. 11 illustrates an example computer display, in this case depicting 4 image display frames, each displaying an image from a different series. The four example series are from a brain MRI exam. In the example shown, each series represents a series of images at sequential spatial positions within the patient, in this example covering the brain. In other embodiments, the series may come from the same or different exams and may be acquired from a variety of imaging modalities, e.g., MRI, CT, ultrasound, nuclear medicine, computed radiography, angiography, etc.

Superimposed on each image is an icon depicting a white circle with 4 lines extending inwardly. This icon represents a 3D cursor icon, with the position of the center of the icon representing the same 3D spatial position within each of the series. The user can reposition the 3D cursor icon in any image, for example by positioning the mouse cursor (shown as an arrow) over the 3D icon, clicking the left mouse button, and moving the mouse. Repositioning the 3D cursor icon in any image automatically causes the 3D cursor to be repositioned into the corresponding 3D position within the other series. This may result in display of a different image within other series that corresponds to the new position of the 3D cursor. For example, moving the 3D cursor inferiorly in the sagittal plane, for example within the "T1 +Gd Sagittal" series displayed in the upper-left frame, would result in display of a more inferiorly located axial image within the "T1 +Gd Axial series" and would result in automatic repositioning of the displayed 3D cursor superimposed on the coronal series. Moving the 3D cursor posteriorly within the axial plane would result in display of more posteriorly positioned images within the coronal series, in this example the "T2 Coronal" and "T1 +Gd Coronal" series.

This is an example of linked series, where changing the displayed image in one series automatically changes the displayed image in another series.

Systems and methods described herein may be applied to the case of linked series where preloading and/or preprocessing of images in each series may be prioritized to improve the responsiveness of the system in response to user interaction.

Multiple Image Series from a 3D Volume

In some cases linking of series may occur across two or more different medical imaging exams that may be obtained with the same or different imaging modalities. For example, series from MRI exams obtained at two different dates may be linked, series from an MRI and a CT may be linked, series from CT and Positron Emission Tomography (PET) exams may be linked, etc. Linking of different exams may be performed by cross registering the exams in 3D using techniques known in the field.

Figure 12:
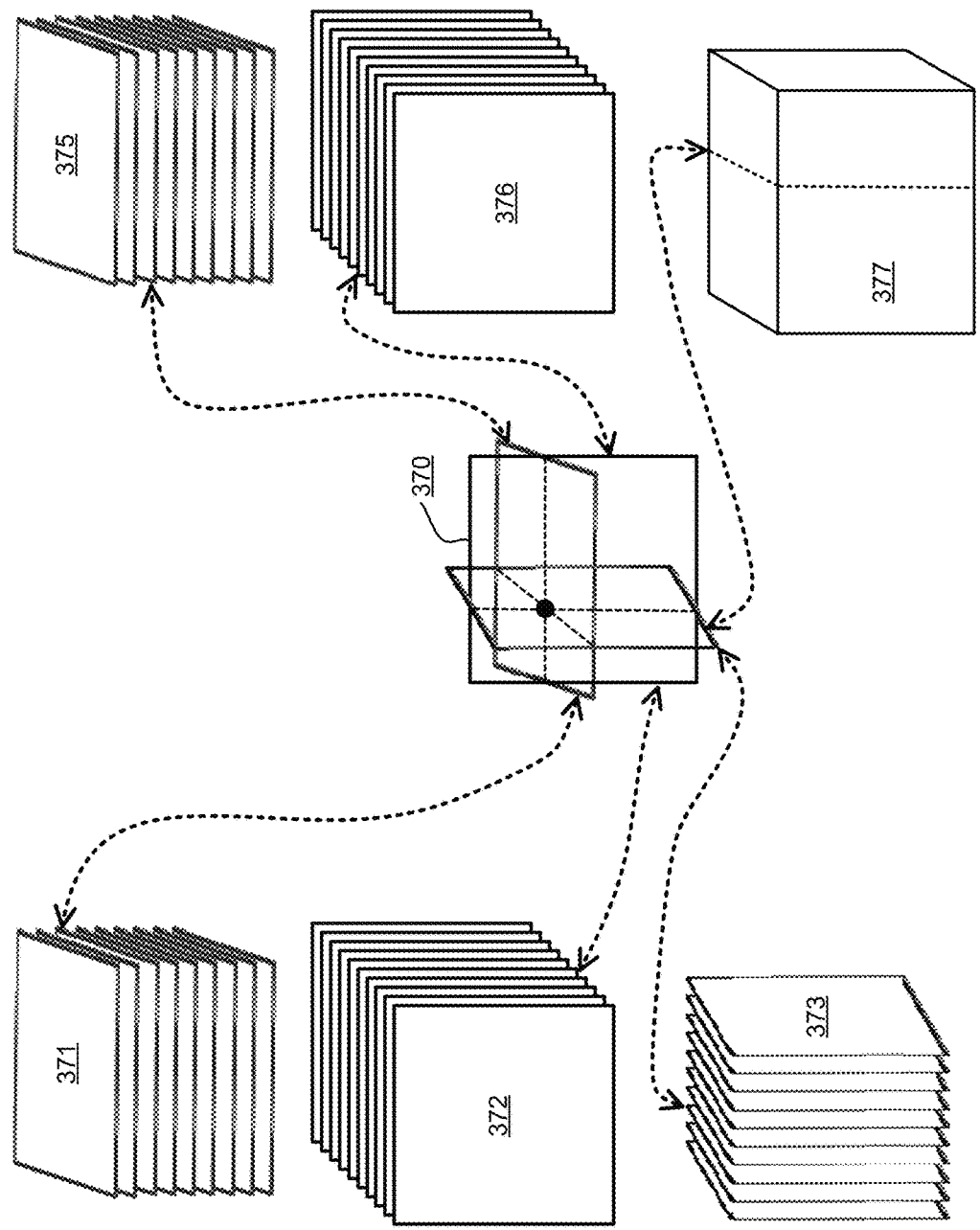
FIG. 12 illustrates intelligent preloading or preprocessing of images of certain image series while also intelligently generating image reconstruction images of other image series (e.g., a 3d volume) in order to provide the user with quicker access to images of multiple series of different types.

In the example of FIG. 12, one exam comprises series 371, 372, and 373, each including a series of 2D images. A second exam comprises series 375, 376 and 377, where series 375 and 376 are series of 2D images and series 377 is a volumetric exam. Using techniques well known in the field, such as multiplanar reconstruction (MPR) it is possible to reconstruct 2D images in any plane from volumetric exams.

Systems and methods described herein may be used to manage images from more than one exam.

Systems and methods described herein can be used to predict which reconstructions, for example MPR reconstructions, are likely to be needed next and create them in advance of the user displaying them.

Further Optimizing Processing

In some embodiments, a processing model may be associated with a portion of an image series (rather than an entire image series). For example, a processing model may not be relevant to the user's viewing of a first few images of an image series (e.g., a radiologist may very quickly scan through the entire image series when first viewing the image series, which is not indicative of his behavior in viewing the images as he performs his detailed analysis). Thus, in one embodiment the processing model may not be used to determine preloading order (or other processing) for an image series until a certain number of images have already been processed, a certain time since opening the image series has passed, and/or a user indicates that the processing model should be initiated. For example, a processing model may be used to determine images to decompress only after a predetermined number of images of the image series have already been processed.

In one embodiment, multiple processing models may be used with a single image series (or other set of images). For example, the first processing model may be initially used when an image series is selected for display, while a second processing model is used for all subsequent processing of the image series. For example, a user may have an initial viewing behavior that is different than a viewing behavior associated with detailed review of images. Thus, the first processing model may be used when the user initially selects an image series for display. The second processing model may be selected after a certain time has passed and/or a certain quantity or portion of images have been displayed (or otherwise processed).

In one embodiment different processing models are associated with different portions of an image series, such as with different anatomical portions of the image series. For example, an abdomen MRI typically images multiple organs. However, a radiologist may have a different viewing behavior while reviewing images of different organs within the same image series. Thus, in one embodiment a first processing model may be used while the user is viewing kidneys, while a second processing model may be used while the user is viewing the pelvis within an abdomen MRI image series. Depending on the embodiment, a processing model may be selected based on various criteria. For example, a particular type of image series (e.g., an image series of a particular modality and/or having one or more particular characteristics) may be associated with a mapping that indicates which processing model to use for different portions of the image series. For example, for an image series of a first type, the mapping may indicate that a first processing model is used for a first 5% of the images of the image series, while a second processing model is used for the remaining 95% of the images of the image series. In one embodiment, the mapping is associated with anatomical features (e.g., organs) that should be present in images of a particular image series. Thus, such a mapping may be used to associate a particular processing model with a particular portion of an image series having an associated anatomical feature. In the example above, the system may determine that in an abdomen MRI image series, images of the kidneys are in a particular portion of a image series. Thus, when processing of images within that portion of the image series is requested, the system may use the particular processing model associated with the kidney portion of image series.

In some embodiments, anatomical features within an image series are indicated in metadata associated with the images, such as DICOM header information. For example, metadata may indicate that at a particular image number, a specific anatomical feature begins. Thus, in embodiments where the system has a different processing model associated with that specific anatomical feature, that different processing model may be selected when that particular image number is selected for processing (or images near that particular image or anatomic location are selected for processing).

In some embodiments, processing models are generated in a manner that disregards viewing behaviors that are outside of an overall viewing behavior. For example, if the user has a certain behavior only during the first few seconds of viewing an image series of a particular type, which is much different than the user's behavior during the remaining several minutes of viewing of image series of that particular type, the user viewing behavior associated with those first few seconds may not be included in the model generation process. In other words, the processing models may be generated using statistical analysis that does not consider statistical outliers.

While processing models may be generated based the viewing behaviors of users, in some embodiments processing models are generated in other ways. For example, a processing model could be manually defined by a user. Other Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for processing images, the method comprising:
by one or more computer processors configured to execute software instructions:
receiving a request for display of a first image series comprising a plurality of images;
determining a characteristic of the first image series;
monitoring behavior of a user in displaying images of the first image series, including recording behavior data indicating an order in which images of the first image series are accessed by the user;
analyzing the behavior data in order to determine a model usable to predict respective probabilities of images of the first image series at various adjacency offsets from a particular image of the first image series being needed next after selection or display of the particular image;
associating the model with the characteristic of the first image series;
determining that a characteristic of a second image series matches the characteristic of the first image series, the second image series including a sequence of a first image and a second image;
determining, based on the model, a set of probabilities related to the second image series, wherein the set of probabilities indicates, for each particular image of at least some images of the second image series, probabilities of images of the second image series at various adjacency offsets from the particular image being needed next after selection or display of the particular image; and
based at least in part on the set of probabilities related to the second image series, processing the first image of the second image series and the second image of the second image series out of sequence.

2. The method of claim 1, wherein more than one of the images of the first image series has a same respective probability of being needed next after selection or display of the particular image.

3. The method of claim 1, wherein the model indicates that a first image of the first image series having a higher adjacency offset than a second image of the first image series is more likely to be needed within the predetermined time period.

4. The method of claim 1, wherein the characteristic of the first image series comprises at least one of: exam type, modality, clinical information, clinical history of a patient, region of body depicted in the first image series, technical parameter of the first image series, or an indication of whether the plurality of images were obtained with or without intravenous contrast.

5. The method of claim 1, wherein the characteristic of the first image series comprises a technical parameter of the first image series, and wherein the technical parameter comprises at least one of: series type, an indication of whether the first image series is a 2D or a volumetric acquisition, slice thickness, resolution, image size, or image type.

6. The method of claim 1, wherein the characteristic of the first image series comprises a series type of the first image series, and wherein the series type comprises at least one of: primary acquisition, MPR (multiplanar reconstruction), MIP (maximum intensity projection), or 3D volume rendering.

7. The method of claim 1, wherein the model is further associated with a characteristic of the user including at least one of: a user identity, a user group of the user, or a user role of the user.

8. The method of claim 1 further comprising:
by the one or more computer processors configured to execute the software instructions:
determining, based on the set of probabilities, one or more images of the second image series to preload into a local memory of a display device.

9. The method of claim 8 further comprising:
by the one or more computer processors configured to execute the software instructions:
determining which of the one or more images to preload are already stored in the local memory; and
initiating preloading of any of the one or more images to preload that are not already stored in the local memory.

10. The method of claim 1 further comprising:
by the one or more computer processors configured to execute the software instructions:
preprocessing, based on the set of probabilities, images of the second image series.

11. The method of claim 10, wherein preprocessing images of the second image series comprises:
based on the set of probabilities, preloading images of the second image series that have been processed into a local memory of a display device.

12. The method of claim 10, wherein preprocessing images of the second image series comprises at least one of: decompressing, performing computer aided diagnosis, or reconstructing images of the second image series.

13. The method of claim 10, wherein preprocessing images of the second image series comprises reconstructing images, and wherein reconstructing images comprises at least one of: MPR (multiplanar reconstruction), MIP (maximum intensity projection), or 3D volume rendering.

14. A method for processing images, the method comprising:
by one or more computer processors configured to execute software instructions:
receiving a request for display of a first image series comprising a plurality of images;
determining a characteristic of a first display device upon which images of the first image series are displayed;
monitoring behavior of a user in displaying images of the first image series, including recording behavior data indicating an order in which images of the first image series are accessed by the user;
analyzing the behavior data in order to determine a model usable to predict respective probabilities of images of the first image series at various adjacency offsets from a particular image of the first image series being needed next after selection or display of the particular image;
associating the model with the characteristic of the first display device;
determining that a characteristic of a second display device upon which images of a second image series are to be displayed matches the characteristic of the first display device, the second image series including a sequence of a first image and a second image;
determining, based on the model, probabilities of images of the second image series at various adjacency offsets from a particular image of the second image series being needed next after selection or display of the particular image of the second image series; and
based at least in part on the set of probabilities related to the second image series, processing the first image of the second image series and the second image of the second image series out of sequence.

15. The method of claim 14, wherein the characteristic of the first display device comprises at least one of: a type of the first display device, a size of the first display device, a number of displays associated with the first display device, an amount of memory of the first display device, or a speed of transmission to the first display device.

16. The method of claim 14 further comprising:
by the one or more computer processors configured to execute the software instructions:
determining, based on the model, one or more images of the second image series to preload into a local memory of a display device.

17. The method of claim 16 further comprising:
by the one or more computer processors configured to execute the software instructions:
determining which of the one or more images to preload are already stored in the local memory; and
initiating preloading of any of the one or more images to preload that are not already stored in the local memory.

18. The method of claim 14 further comprising:
by the one or more computer processors configured to execute the software instructions:
preprocessing, based on the model, images of the second image series.

19. The method of claim 18, wherein preprocessing images of the second image series comprises:
based on the model, preloading images of the second image series that have been processed into a local memory of a display device.

20. The method of claim 18, wherein preprocessing images of the second image series comprises at least one of: decompressing, performing computer aided diagnosis, or reconstructing images of the second image series.

* * * * *